United States Patent
Kelly et al.

(10) Patent No.: US 8,753,568 B2
(45) Date of Patent: Jun. 17, 2014

(54) AUTONOMOUS DEVICE WITH BIOFOULING CONTROL AND METHOD FOR MONITORING AQUATIC ENVIRONMENT

(76) Inventors: Vincent M. Kelly, Easton, MD (US); Louis Anthony Codispoti, Oxford, MD (US); Steven Edward Suttles, Cambridge, MD (US)

( * ) Notice: Subject to any disclaimer, the term of this patent is extended or adjusted under 35 U.S.C. 154(b) by 0 days.

(21) Appl. No.: 12/986,048

(22) Filed: Jan. 6, 2011

(65) Prior Publication Data
US 2013/0018491 A1    Jan. 17, 2013

Related U.S. Application Data

(63) Continuation-in-part of application No. 12/187,787, filed on Aug. 7, 2008, now Pat. No. 8,038,937.

(60) Provisional application No. 60/954,412, filed on Aug. 7, 2007.

(51) Int. Cl.
*B08B 17/00*    (2006.01)

(52) U.S. Cl.
USPC ............... 422/6; 422/40; 422/114; 422/116; 422/275; 73/170.29

(58) Field of Classification Search
USPC ................. 422/6, 40, 114, 116, 261, 265, 422/268–271, 275, 277; 73/170.29, 170.34
See application file for complete search history.

(56) References Cited

U.S. PATENT DOCUMENTS 4,763,537 A * 8/1988 Scott et al. ................. 73/170.29

* cited by examiner

*Primary Examiner* — Timothy Cleveland
(74) *Attorney, Agent, or Firm* — Christopher Aniedobe, Esq.

(57) ABSTRACT

A microprocessor preprogrammable autonomous device with biofouling control and method for monitoring aquatic environment by disposing environmental sensors in a sensor chamber which programmably opens for allowing direct communication between the sensors and the fluid of interest for sampling and which is closed after the sampling sequence is completed to create an anti-fouling environment in the sensor chamber by dissolving a biocide salt in the chamber and exposing the sensors to the anti-fouling environment for a predetermined period of time.

20 Claims, 23 Drawing Sheets

Detail A

Detail B

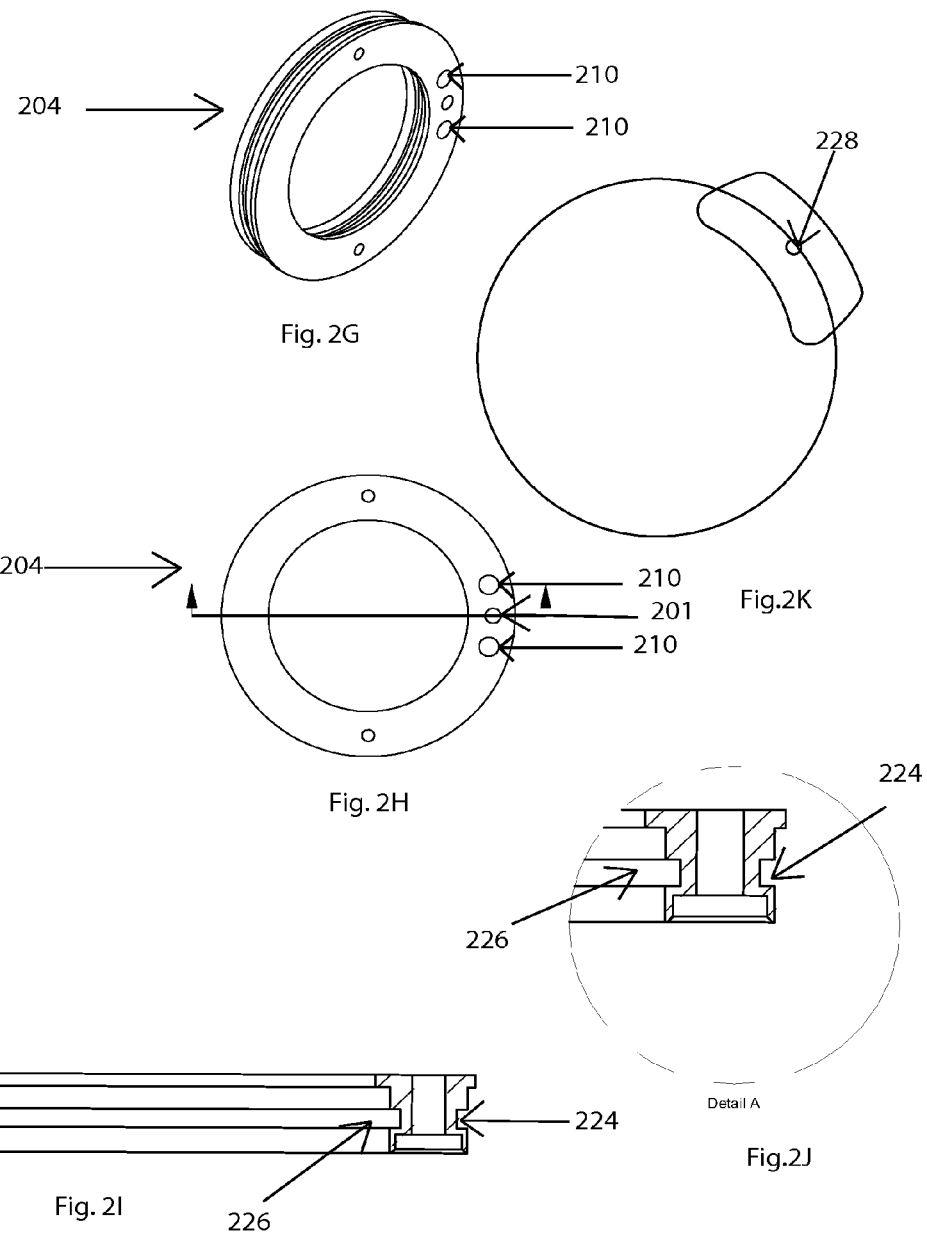

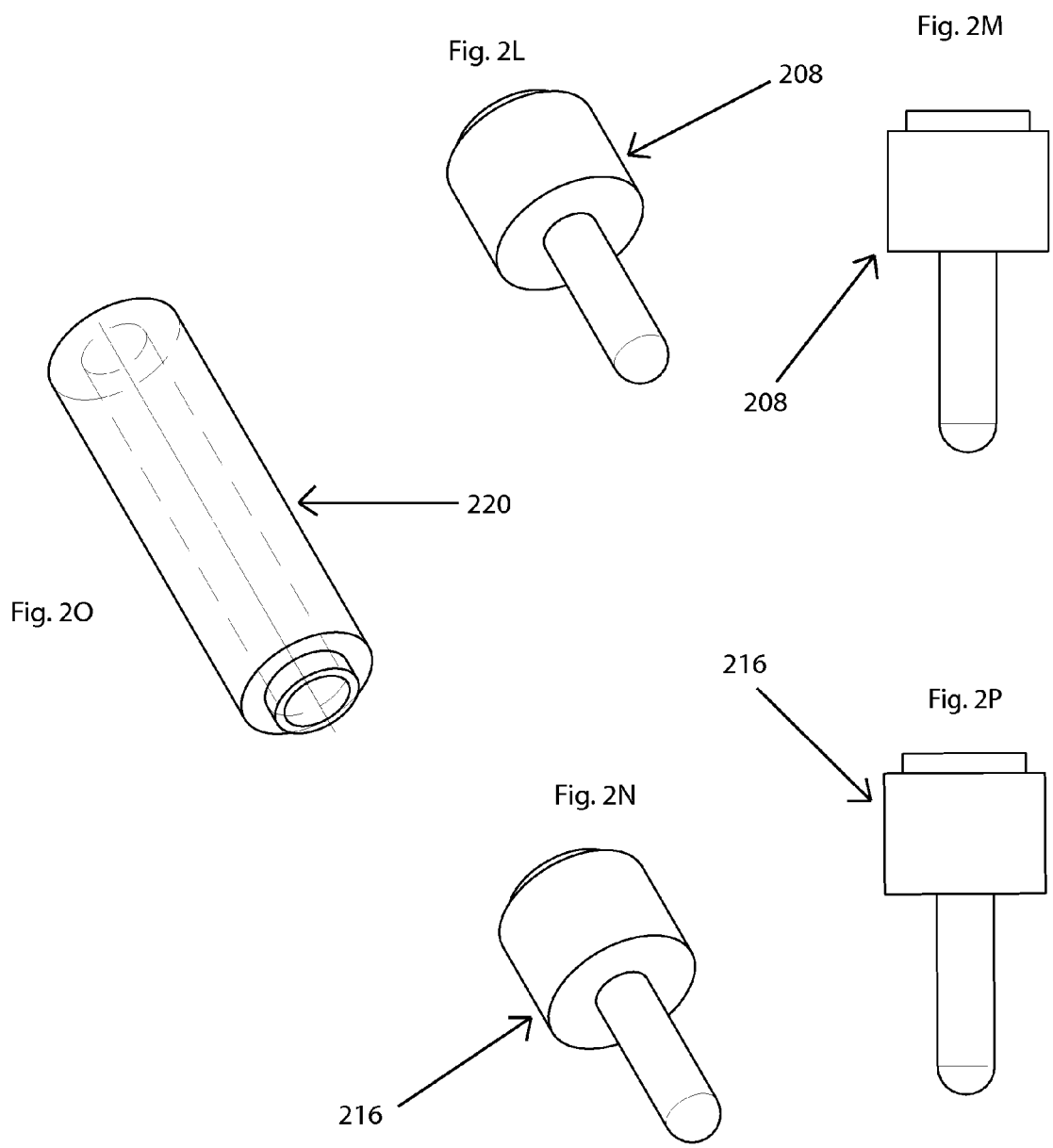

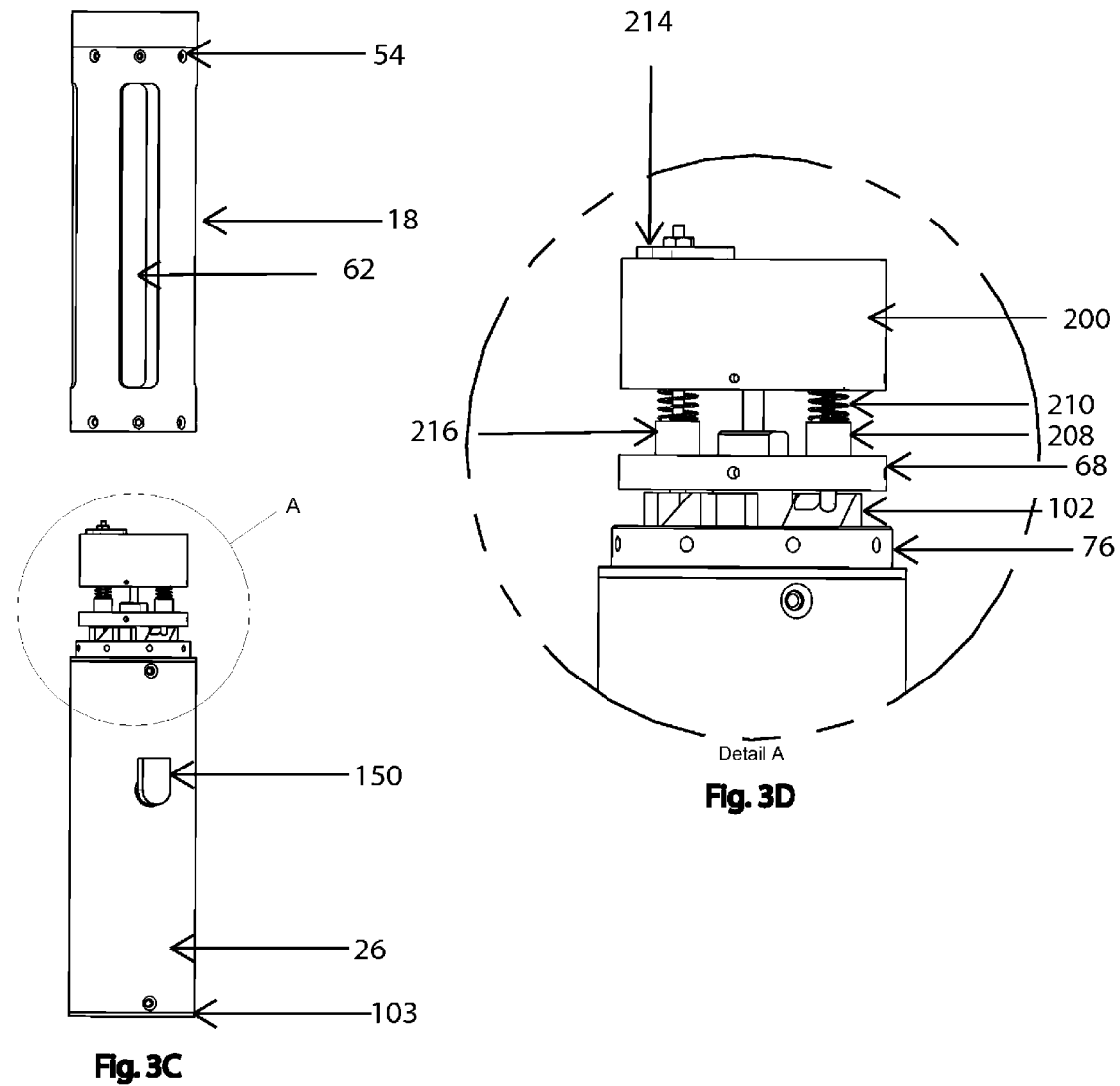

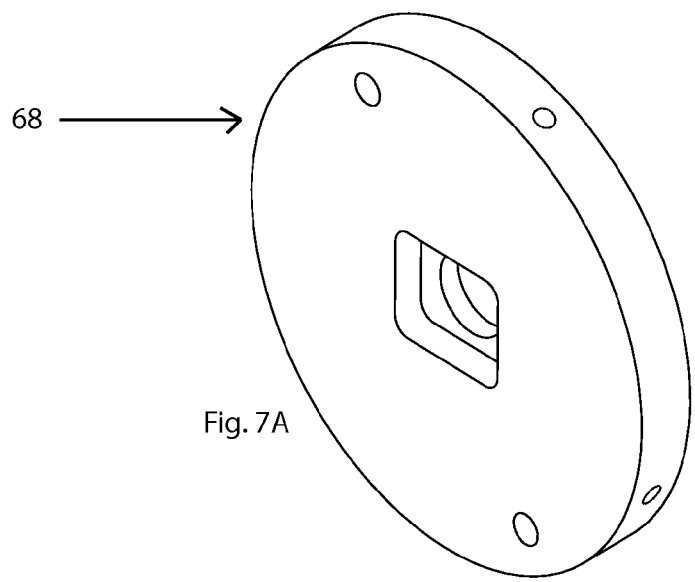
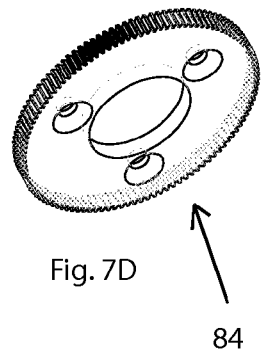
Fig. 7A
Fig. 7D
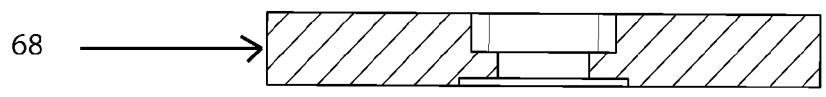
Section A-A    Fig. 7B
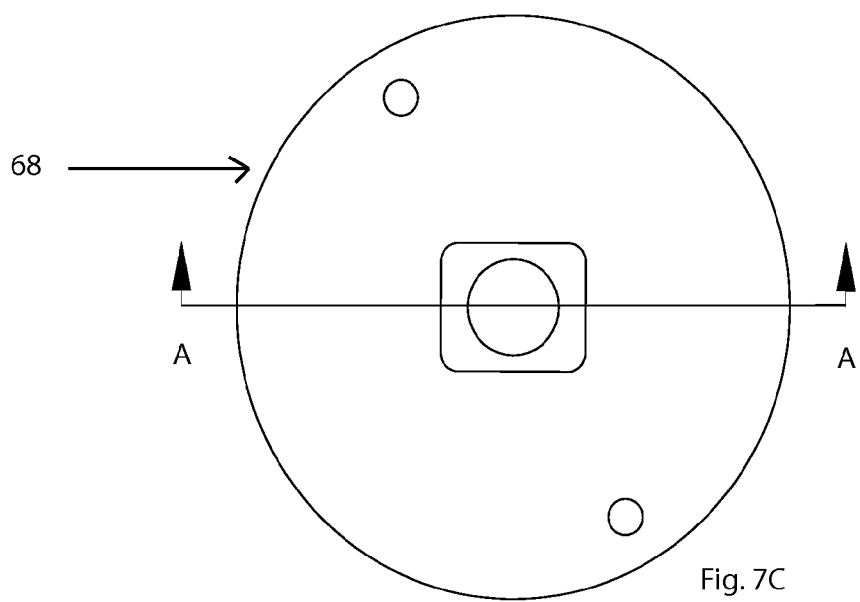
Fig. 7C

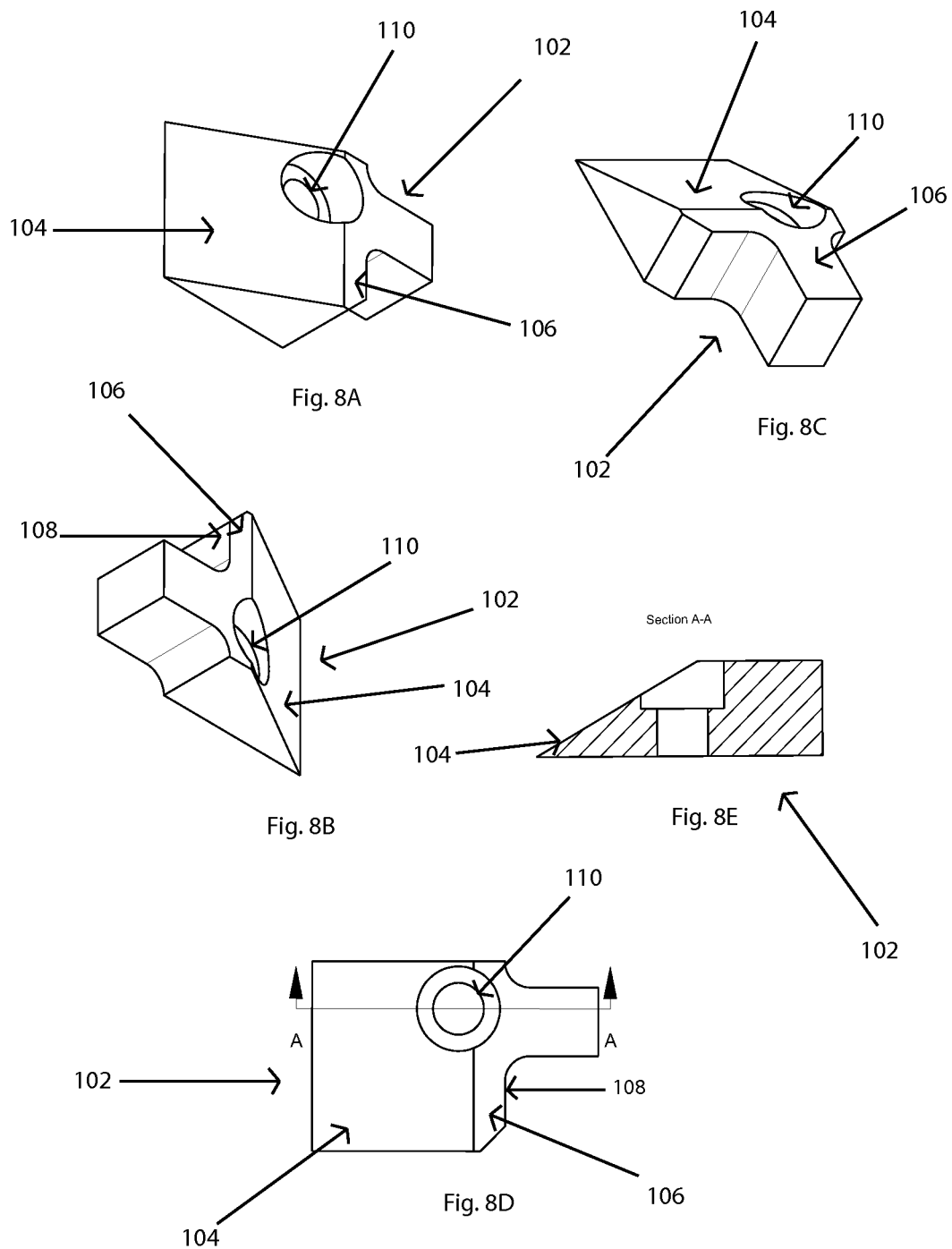

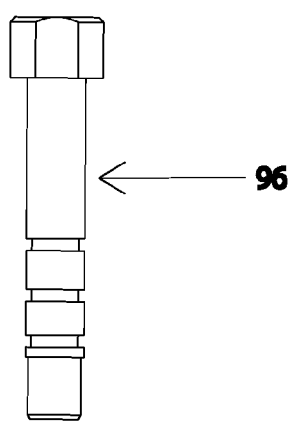
Fig. 9A
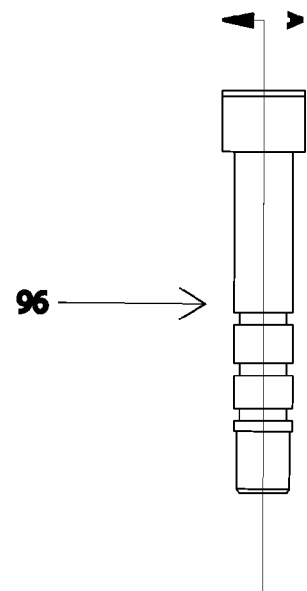
Fig. 9D
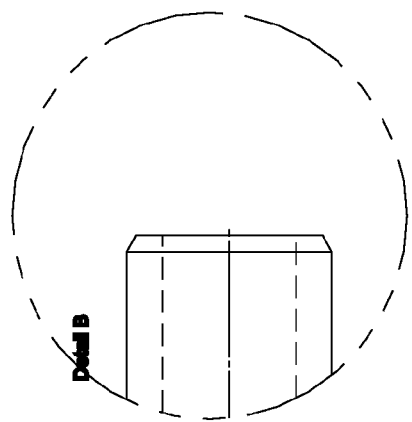
Fig. 9F
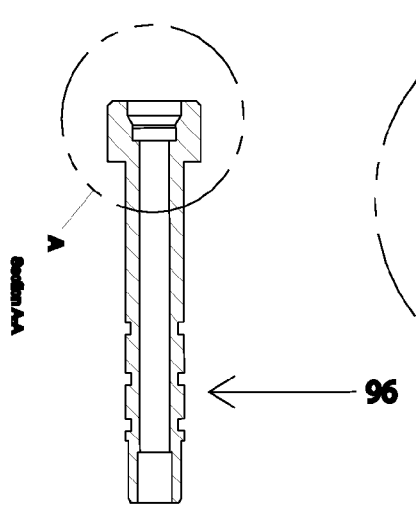
Fig. 9B
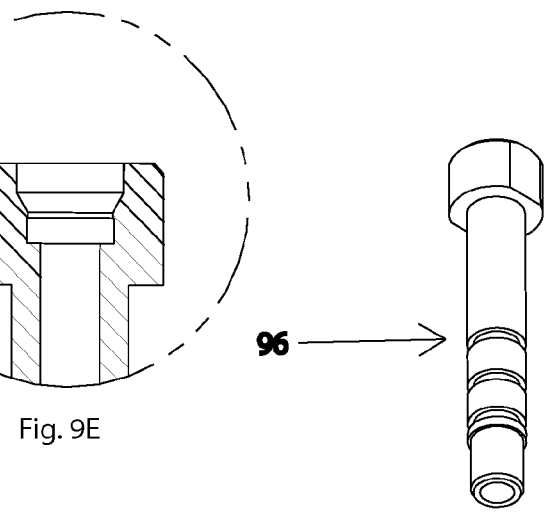
Fig. 9E
Fig. 9C

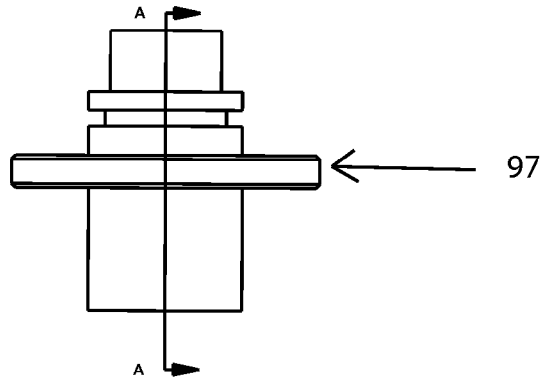
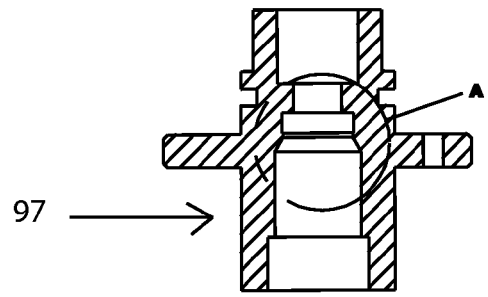
Fig. 10A
Fig. 10B
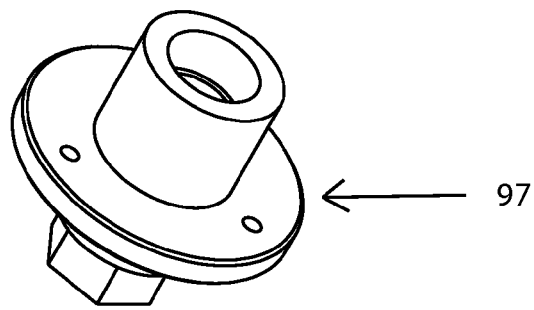
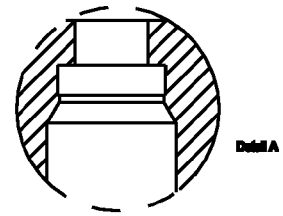
Fig. 10C
Fig. 10D
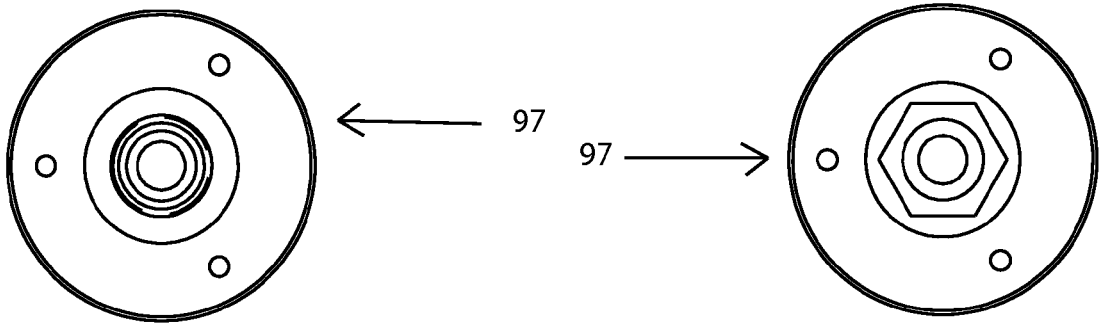
Fig. 10E
Fig. 10F

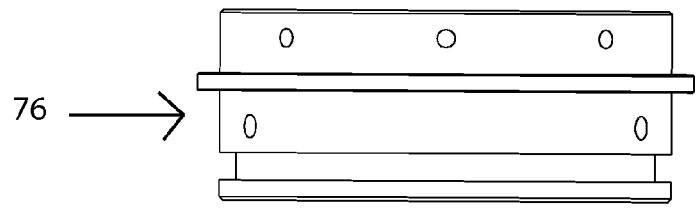
Fig. 14A
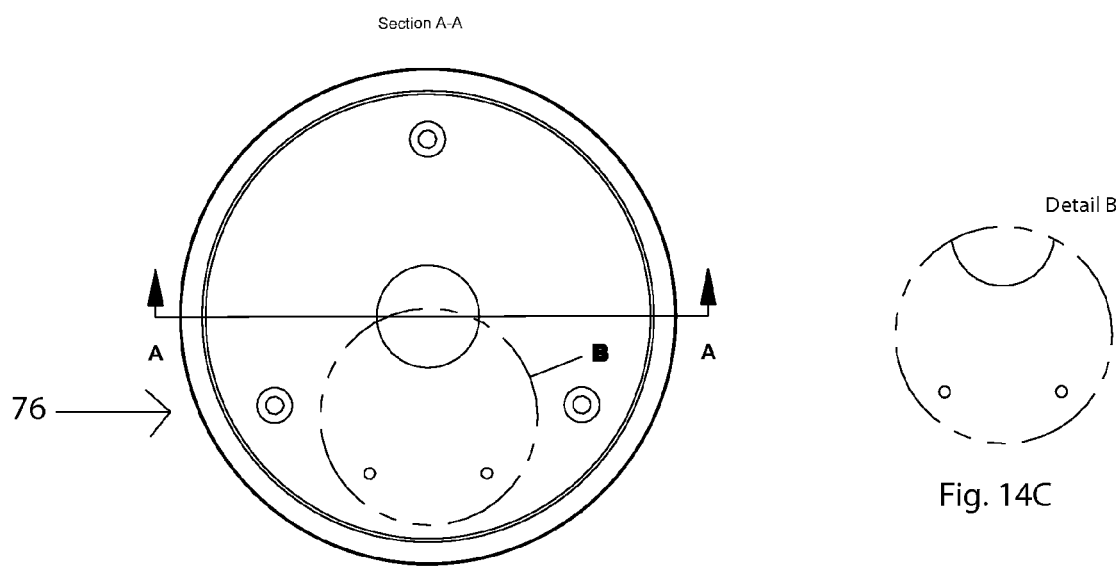
Fig. 14B
Fig. 14C
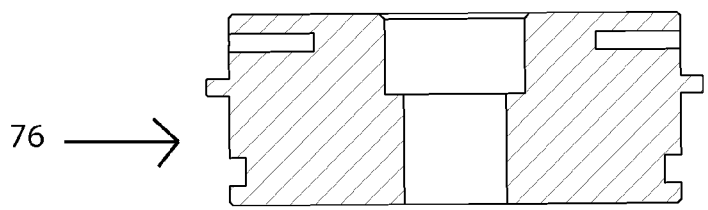
Fig. 14D

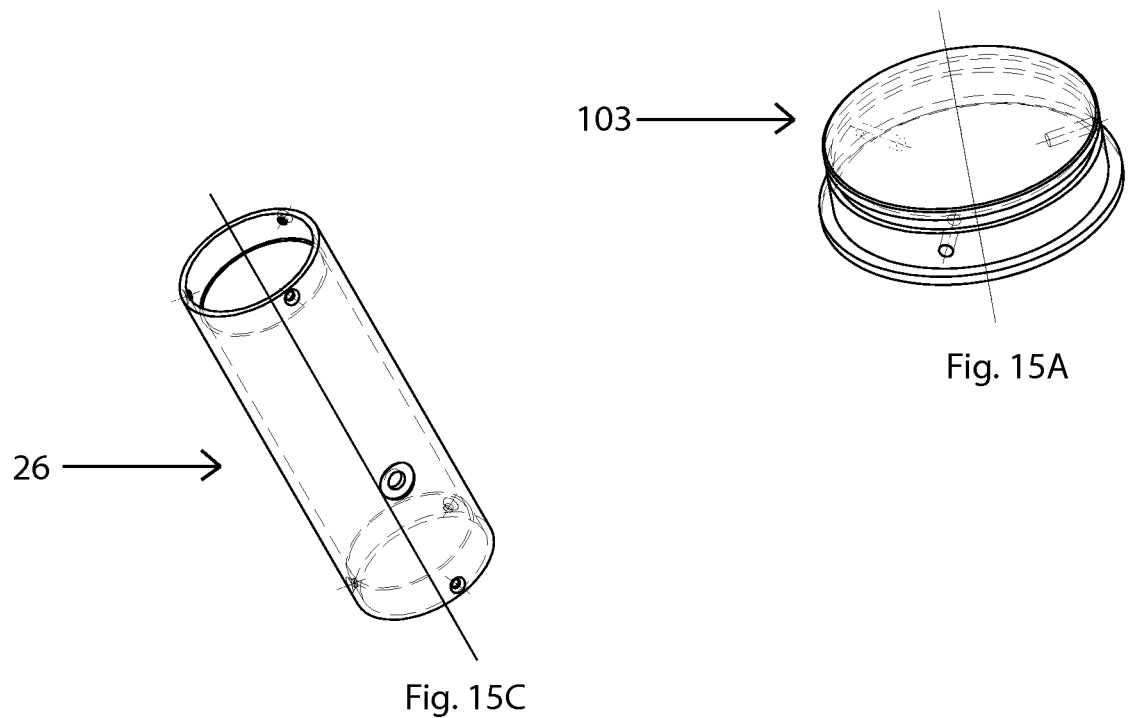
Fig. 15A
Fig. 15C
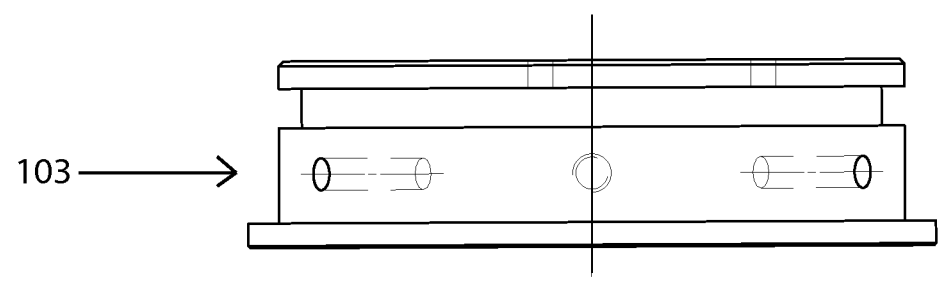
Fig. 15B

AUTONOMOUS DEVICE WITH BIOFOULING CONTROL AND METHOD FOR MONITORING AQUATIC ENVIRONMENT

REFERENCE TO RELATED APPLICATIONS

This application is a Continuation-in-Part of U.S. patent application Ser. No. 12/187,787, filed Aug. 7, 2008, which claims priority to U.S. Provisional Patent Application 60/954,412 filed Aug. 7, 2007; the entire contents of which are incorporated herein by reference.

FIELD OF THE INVENTION

The present invention is directed to biofouling resistant apparatus and method for monitoring of fluid (aquatic and gaseous) environments, and particularly to pre-programmable autonomous devices with anti-biofouling capabilities deployed in aquatic environment for acquisition of data related to chemical, biological and physical conditions of the environment of interest.

BACKGROUND OF THE INVENTION

There is an ever increasing interest in the deployment of autonomous devices for monitoring biological, chemical and physical conditions in aquatic environments. This interest encompasses monitoring hydrographic conditions, fisheries, weather prediction, and global change in the open ocean. It also includes estuaries where interest arises from concerns about pollution, harmful algal blooms, living resources and biological diversity.

Reflecting the need for autonomously collected data, the advances in technology have produced reasonably affordable instrumentation capable of collecting and telemetering data. However, biofouling remains a major problem that to date has not been adequately addressed. The amount of growth that can accumulate in and around sensors over periods as short as 5 days can be great in high nutrient estuarine environments. Biofouling is, for a large percentage of instrumentation deployments, the single biggest factor affecting the operation, maintenance, and data quality of in-water monitoring sensors, and therefore biofouling prevention for sensor systems is considered a major issue in aquatic environment monitoring.

The scientific community recognizes that not only should sensors of monitoring devices be protected from biofouling, but additionally the environment surrounding the sensors must also be protected since in some cases, fouling can become so extreme that one can question whether the sensors are sampling the ambient water or a microenvironment controlled by the activities of the fouling organisms.

The biofouling of ships and instrumentation is typically controlled through the use of toxic paints incorporating metal biocides, e.g. cuprous oxide, and organometals, e.g. tributyltin. Anti biofouling paints cannot be put directly on the sensors and may not be sufficiently soluble to provide a "halo" effect that will protect the sensors. In addition, anti-biofouling paints can sometimes accumulate films that could inhibit sensor performance, after short periods of immersion. Also, mechanical systems, such as anti-fouling wipers have been developed and used in multi-parameter monitor devices. However, the anti-fouling paints are extremely toxic and thus are harmful for living organisms, while wipers do not have the capability of complete prevention and removal of bio-fouling, thereby only partially addressing the bio-fouling problem. These wipers can also become substrate for fouling organisms and thus scratch optically clear surfaces.

Usually, deployed instrumentation is serviced weekly or biweekly (depending on a region and season) to remove deposits of bio-organisms from the sensors or to replace the deployed sensors with cleaned and recently calibrated sensors. This is a time and cost consuming endeavor which makes aquatic environments monitoring extremely expensive and labor intensive.

There is therefore a need and ever increasing interest in monitoring of chemical and physical conditions in aquatic environments to provide autonomous devices capable of extended instrument deployment and of obtaining uncorrupted data by controlling the biofouling and eliminating the effect of biofouling on device operations.

SUMMARY OF THE INVENTION

Accordingly, the present invention is directed to biofouling resistant programmable autonomous monitoring device deployed in an aquatic environment by means of periodically exposing deployed environmental sensor(s) to a biocide environment after a programmable sampling sequence is completed by the sensor(s), thereby protecting the immediate surrounding of the sensors from biofouling formation. Sampling time is followed by an anti-fouling treatment time period during which the immediate surrounding of sensor is filled with anti-fouling biocide uniformly dispersed therein. A preprogrammed controller (microprocessor) in the autonomous device controls operation of mechanical/electrical mechanisms of the autonomous device in synchrony with the sensors' sampling cycle and biocide release. Programmable variables include sampling frequencies, biocide dispense times and amounts, etc., as well as modalities for remote data acquisition system.

It is one object of the present invention to provide a device with bio-fouling control for autonomous monitoring of a fluid environment, comprising: at least one sensor unit operationally controllable to operate in accordance with a predetermined sampling cycle, the sampling cycle including at least one sampling time period followed by an anti-fouling treatment time period, a sensor envelope positioned in a surrounding relationship with the at least one sensor unit and defining a chamber containing the at least one sensor unit, at least one source of an anti-fouling matter contained in the chamber the source of anti-fouling matter comprising an outer sleeve and at least one inner sleeve arranged substantially concentric with respect to the outer sleeve and having a closable upper end and a closed lower end which establish an annular reservoir space filled with biocide matter, the source further comprising a biocide outlet means and vent in fluid communication with the chamber, and a preprogrammed control unit operatively coupled to the sensor envelope and the at least one source of the anti-fouling matter, wherein the preprogrammed control unit actuates the sensor envelope to provide fluid communication between the at least one sensor unit and a fluid during the at least one sampling time period, and further activates the at least one source of the anti-fouling matter to create an anti-fouling environment in the chamber during the anti-fouling treatment time period.

The sensor envelope comprises a housing having at least one window, the at least one window being opened, under control of the preprogrammed control unit, during the at least one sampling time period to permit the fluid inside the sensor envelope in contact with the at least one sensor unit, and wherein the at least one window is controllably closed during the anti-fouling treatment time period to maintain the anti-fouling environment inside the sensor envelope.

It is another object of the present invention to provide a device with bio-fouling control for autonomous monitoring of aquatic environments wherein the preprogrammed control unit synchronizes opening/closing of at least one window of the housing with the controllable release of the biocide matter in the chamber.

In one embodiment, the housing comprises an outer cup and an inner cup positioned in concentric relationship with the outer cup, the outer cup having an outer cup wall and a plurality of outer cup openings formed at predetermined positions on the outer cup wall, and the inner cup having an inner cup wall and a plurality of inner cup openings formed at predetermined positions on the inner cup wall, the inner and outer cups having a first relative disposition during the at least one sampling time period and a second relative disposition during the anti-fouling treatment time period, wherein in the first relative disposition between the inner and outer cups, respective ones of the plurality of inner cup openings and of the plurality of outer cup openings are positioned to overlap each other, and wherein in the second relative disposition between the inner and outer cups, the respective inner cup and outer cup openings are displaced each from the other in a controlled manner.

In another embodiment, during the anti-fouling treatment time period, the displacement between the respective inner cup and outer cup openings is synchronized with the release of the biocide matter by the preprogrammed control unit.

In another embodiment, the device further comprises an actuation unit operatively coupled to either of the inner and outer cups to establish a respective one of the first and second relative dispositions therebetween in accordance with instructions received from the preprogrammed control unit and wherein the control unit further includes a microprocessor preprogrammed prior to deployment of the device in the fluid environment.

In another embodiment, the device further comprises a non-volatile memory, wherein data obtained from the at least one sensor unit is stored in the non-volatile memory under control of the preprogrammed microprocessor and wherein the device further includes an interface port, the data being dispatched periodically from the non-volatile memory to a telemetry and data collection system via a communication link established between the device and the telemetry and data collection system.

It is yet another object of the present invention to provide a device with bio-fouling control for autonomous monitoring of aquatic environments comprising a first and second co-axial supporting disks positioned in the chamber and rotationally displaceable about an axis thereof, the first and second co-axial supporting disks being spaced each from the other along the axis, wherein the inner cup is mounted on the first supporting disk, and wherein the outer cup is mounted on the second supporting disk, a plurality of ramp units positioned circumferentially on a surface of the second supporting disk a predetermined distance each from another between the first and second supporting disks; and a vent and valve mechanism mounted on the first supporting disk in a controllable contact with the at least one source of the anti-fouling matter, the valve mechanism being actuated by interaction with a respective one of the plurality of ramp units in accordance with a relative disposition between the first and second supporting disks to control opening of the vent or valve when the first and second co-axial supporting disks are rotationally displaced under control of the preprogrammed control unit.

In one embodiment, the device further comprises a flushing unit inside the chamber operating to remove the anti-fouling environment therefrom upon completion of the anti-fouling treatment time period prior to the at least one sampling time period.

In another embodiment, the device further comprises a casing connected to the sensor envelope at one end thereof, the casing having an internal cavity fluidly separated from the chamber of the sensor envelope, batteries and an actuator mechanism received within the internal cavity of the casing, and wherein the preprogrammed controller is received in the casing. The pressure casing for accommodating mechanical and electrical/electronic parts and batteries, as well as receives a printed circuit board with electronics necessary for operation of the device.

It is yet another object of the invention to provide a method for bio-fouling control of an autonomous device for monitoring a fluid environment, comprising the steps of: forming a sensor envelope for at least one sensor unit, positioning the at least one sensor unit into a chamber defined within the sensor envelope, programming a control unit prior to deployment of the autonomous device in the fluid environment, deploying the autonomous device having the preprogrammed controller unit embedded therein in the fluid environment, opening the chamber to the fluid environment under control of the preprogrammed control unit to establish fluid communication between a fluid and the at least one sensor unit, sampling the fluid, upon completion of the sampling during at least one sampling time period, closing the chamber, and releasing, under the control of the preprogrammed control unit, at least one biocide matter from a biocide reservoir unit comprising an outer sleeve and an inner sleeve arranged substantially concentric with respect to the outer sleeve and having a closable upper end and a closed lower end which establish an annular reservoir space filled with biocide matter, the reservoir unit further comprising a biocide outlet means and vent in fluid communication with the chamber to create an anti-fouling environment therein, thereby exposing the at least one sensor unit to the anti-fouling environment during an anti-fouling treatment time period.

In one embodiment the method further comprises the steps of: upon completion of the anti-fouling treatment time period, opening the chamber, and replacing the anti-fouling environment in the chamber with the fluid.

In another embodiment, the method further comprises the step of: during the anti-fouling treatment time period, activating stirring of the anti-fouling environment to evenly disperse the at least one biocide matter within the chamber.

In yet another embodiment, the method further comprises the steps of: recording data acquired during the at least one sampling period in a memory block of the autonomous device, establishing a communication link between the autonomous device and a data collection system, and sending the recorded data from the memory to the data collection system for further processing.

In yet another embodiment, the method further comprises the steps of: preprogramming the control unit prior to the deployment of the autonomous device to embed therein operation parameters selected from the group consisting of: sampling frequencies, biocide dispense time, biocide dispense amount, stirring duration of the biocide in the chamber, duration of flushing of the anti-fouling environment from the chamber, duration of the sampling time period, duration of the anti-fouling treatment time period, and parameters for synchronized operation of the autonomous device.

It is yet another object of the present invention to provide a device with bio-fouling control for autonomous monitoring of a fluid environment, comprising: at least one sensor unit operating in accordance with a predetermined sampling cycle including at least one sampling time period followed by an anti-fouling treatment time period, a sensor envelope for the at least one sensor unit, the at least one sensor unit being disposed in a chamber defined by the sensor envelope, at least one biocide reservoir comprising an outer sleeve and inner sleeves arranged substantially multiconcentric with respect to the outer sleeve and having a closable upper end and a closed lower end which establish an annular reservoir space filled with biocide matter, the reservoir further comprising biocide outlet means and vents in controlled fluid communication with the chamber, an actuating unit operatively coupled to the at least one biocide reservoir, and a controller unit controlling the actuating unit in a programmable manner, wherein, during the anti-fouling treatment time period, upon completion of the at least one sampling time period, the actuating unit, under the control of the control unit, activates release of the biocide matter from the at least one biocide reservoir in a controlled fashion through a valve mechanism to create an anti-fouling environment in the chamber, thereby exposing the at least one sensor unit to the anti-fouling environment upon completion of the at least one sampling time period to substantially prevent and eliminate bio-fouling in immediate surrounding of the at least one sensor unit.

One embodiment of the device comprises a sensor envelope (housing or container) surrounding the sensing units, a source of anti-fouling biocide, a control unit (preprogrammed microprocessor) which controllably opens the sensor envelope to create direct communication between the sensors and the fluid matter of interest during the sampling period, and which further closes the sensor envelope and "instructs" the biocide source to release the biocide matter to create an anti-biofouling environment in the sensor envelope during the anti-fouling treatment periods.

Preferably, the source of biocide or anti-fouling matter is a biocide reservoir surrounding a stirring propeller for even dispersal of a dense biocide solution or slurry throughout the closed sampling chamber. In a preferred embodiment, the biocide reservoir comprises an outer sleeve and an inner sleeve arranged substantially concentric with respect to the outer sleeve and having a closable upper end and a closed lower end which establish an annular reservoir space filled with biocide matter, the reservoir further comprising a biocide outlet means and vent in fluid communication with the chamber. The inner sleeve defines a central opening in the reservoir which is configured and adapted to extend radially around the stirrer blades of the propeller for rapid and even dispersal of the biocide matter.

The toroid shape of this reservoir increases the efficiency of the stirring propeller because it surrounds the propeller as a ducted fan or kort nozzle, and because it incorporates valves that permit ambient water to enter and leave the reservoir, the reservoir can contain a large charge of biocide that is gradually dissolved by ambient water, thus allowing long deployment times. The provision of upper and lower valves to this reservoir permits bubbles that may be formed in the reservoir to be released upwards and a dense charge of biocide infused water to be released downwards. Ambient water enters the reservoir in small amounts during both of these processes and dissolves more biocide that can be released during the next cycle.

The sensor envelope is preferably formed as a housing with one or several windows which are controllably opened/closed in accordance with the sampling cycle of the sensors. The housing may be implemented as a double-wall structure having an outer cup and an inner cup positioned in concentric relationship with each other and each having a plurality of openings of predetermined dimensions, and positioned at predetermined positions on the walls of the inner and outer cups. The controller changes a relative disposition between the inner and outer cups in synchrony with the sampling cycle of the sensors in order to control the relative disposition between the openings on the walls of the inner and outer cups, thereby controlling the extent of "openness/closeness" of the chamber to the aquatic environment.

The device further comprises an actuator unit operationally coupled to either the inner or outer cups to establish a respective relationship therebetween in accordance with the predetermined sampling cycle of the sensing unit(s) under the control of a microprocessor.

The data collected during the sampling periods are written into a nonvolatile memory in the autonomous device and may be periodically dispatched telemetrically, if needed, to a remote data acquisition system for further analysis and processing.

Parameters, such as sampling frequency, biocide dosing frequency (amount), etc., as well as a sequence of operations in the autonomous device, may be embedded into the microprocessor in a laboratory prior to deployment of the monitoring device. The microprocessor which is preprogrammed prior to deployment, controls the sampling cycle of the sensors, as well as relative disposition of the inner and outer cups, in synchrony with biocide release, collects data in the nonvolatile memory, and is further capable of processing the acquired data. A telemetry and data collection system may periodically request instrument data stored on the device's nonvolatile memory. Such data could then be displayed on the Internet for sharing the data with parties interested in such data receipt.

Preferably, when the biocide matter is controllably released in the chamber, the anti-fouling environment is stirred to evenly dispense the biocide matter within the chamber. The stirrer is further run upon completion of the anti-fouling treatment period, opening the chamber, and replacing the anti-fouling environment in the chamber with the fluid matter of interest for the next sampling.

The method of the invention further comprises, a controller (microprocessor) preprogrammed prior to deployment, so that the deployed autonomous monitoring device operates in accordance with the program and operational parameters "embedded" in the microprocessor for an extended deployment period.

The method of the invention further comprises sampling the water by sensors during sampling time intervals and writing the data onto nonvolatile memory within the autonomous device; when needed, establishing a communication link between the autonomous device and a remote computer system, and telemetrically sending the collected data from the memory to the remote computer system for further processing and analysis of the collected data.

These and further objects of the present invention will become evident in view of further disclosure taken in conjunction with accompanying Patent Drawings.

BRIEF DESCRIPTION OF THE DRAWINGS

FIGS. 2G-2K are different perspective views of the biocide reservoir unit's lid of the present invention;

FIGS. 2L, 2M, 2N, 2P, are different views of the vent and valve push pegs of biocide reservoir unit;

FIG. 2O is an illustration of the vent bushing of the biocide reservoir unit;

FIGS. 3A, 3B, 3C, and 3D are representations of the monitoring device in accordance with one embodiment of the present invention;

FIGS. 7A, 7B, 7C, are different perspective views of the inner cup base plate;

FIG. 7D is a representation of a drive gear according to one embodiment of the present invention;

FIGS. 8A-8E represent perspective views of a ramp unit used for control of the biocide release;

FIGS. 9A-9F are perspective views of the outer shaft used to drive the inner cup base plate;

FIGS. 10A-10F are perspective views of the bearing housing;

FIGS. 14A-14D are perspective views of the sampling chamber bulk head of the present invention;

FIG. 15A-15C are perspective views of rear bulk head and pressure housing (FIG. 15C);

DETAILED DESCRIPTION OF THE PREFERRED EMBODIMENTS

Figure 1:
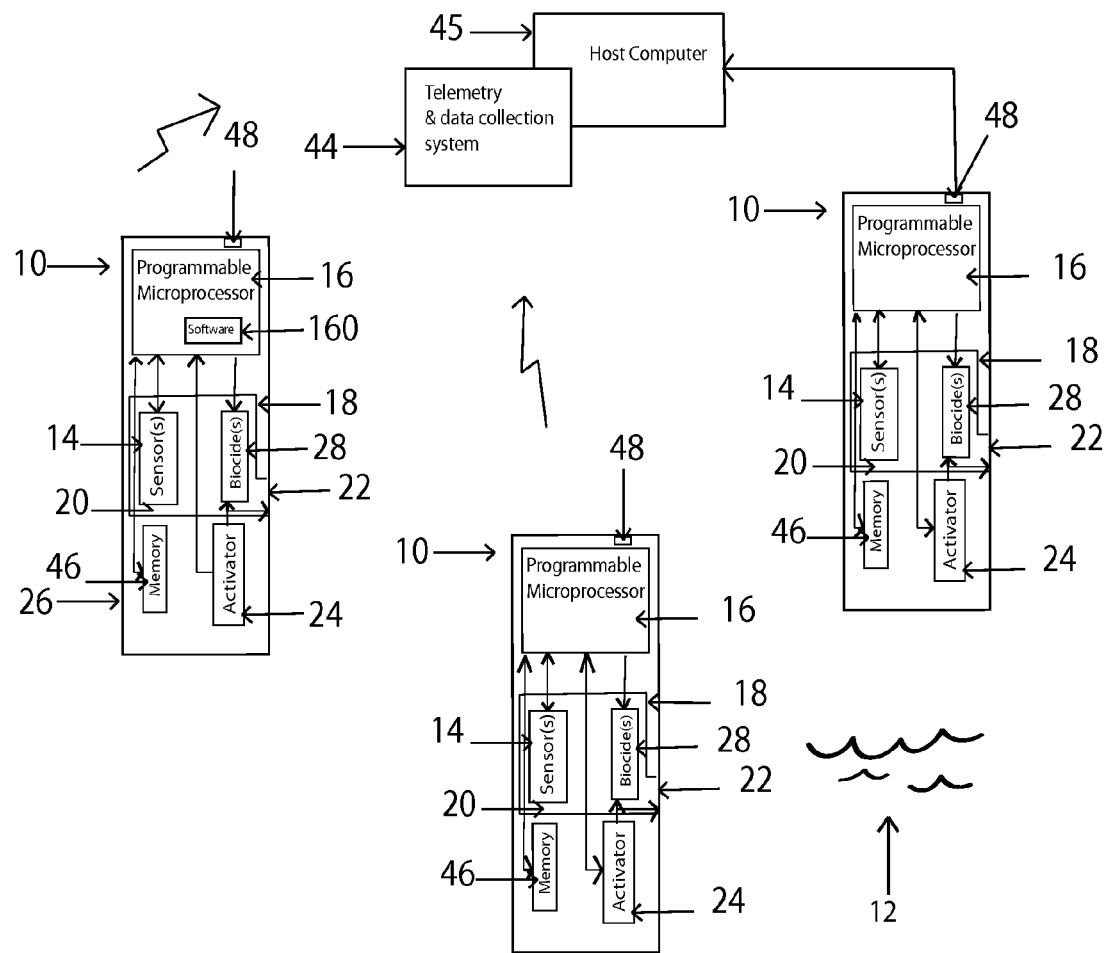
FIG. 1 is a schematic representation of the autonomous monitoring devices of the present invention.

Referring to FIG. 1, a programmable autonomous device 10 is shown with biofouling control for monitoring fluid environment (for example aquatic environment or gaseous environment) 12 and is designed for deployment at a predetermined position in an aquatic environment for an extended period of time. Due to the anti-fouling control, the autonomous device 10 is capable of autonomous operation without the need for servicing for periods of one to several months.

The autonomous device 10 of the present invention may use any number of sensors 14 of a variety of types and is adapted to protect analog or serial sensors for measuring physical and chemical parameters of the water in the aquatic environment 12. As one of many possible examples, a multi-probe sensor instrument may be used with the autonomous device 10 of the present invention, such as multi-parameter Sondes YSI6600 for monitoring dissolved oxygen, chlorophyll, blue-green algae, turbidity, temperature, pH level, etc., although other sensing arrangements are contemplated as well in the scope of the present invention.

Since the autonomous device 10 is deployed for significantly long periods of time, it is preferred that the sensors do not sample the water continuously but operate in accordance with a predetermined sampling cycle which is programmed into the microprocessor 16 of the autonomous device 10, prior to the deployment of device 10. For example, with the YSI6600 multiprobe, the autonomous device 10 may sample water every 15 minutes which is generally regarded as a sufficiently high sample frequency for moored water quality sensors. Other sampling frequencies are envisioned subject to a specific requirement for monitoring the water.

The novel approach devised for anti-fouling control of the autonomous device 10 encompasses the enveloping of the environmental probes (sensors) 14 into a sensor envelope 18 to form a chamber 20 where a concentrated antifouling environment is periodically created to immediately surround the sensors between sampling periods. The sensor envelope 18 may be implemented in various alternative embodiments. As one of the alternative implementations, the sensor envelope 18 includes windows, or shutters, 22 which may be opened and closed via the control of an actuator 24, preferably a DC motor, contained in the electronics and battery housing 26, as will be disclosed in detail in further paragraphs.

Sampling cycles of the sensors 14 include sampling time periods followed by anti-fouling treatment time periods. During a sampling cycle, the shutters 22 are opened, the treated water of the previous cycle is flushed out with a stirrer, while new volume of water enters and fills the sensor envelope. Flushing of the sensor (or sampling) chamber can also be accomplished via natural flow of water through the chamber while the shutters are open. The sensors 14 are instructed by the microprocessor 16 to start sampling during the sampling time period. Upon completion of the sampling, the shutters start closing and "dosing" of the water enclosed in the chamber 20 with one or more biocides 28 begins. The biocide(s) preferably is (are) delivered from a biocide reservoir unit (BRU) in a controlled manner via a valve actuated mechanism as will be disclosed in further paragraphs, although other alternative mechanisms for controlled delivery and dispersion of biocides in the sensor envelope is contemplated in the present device 10.

Figure 2A:
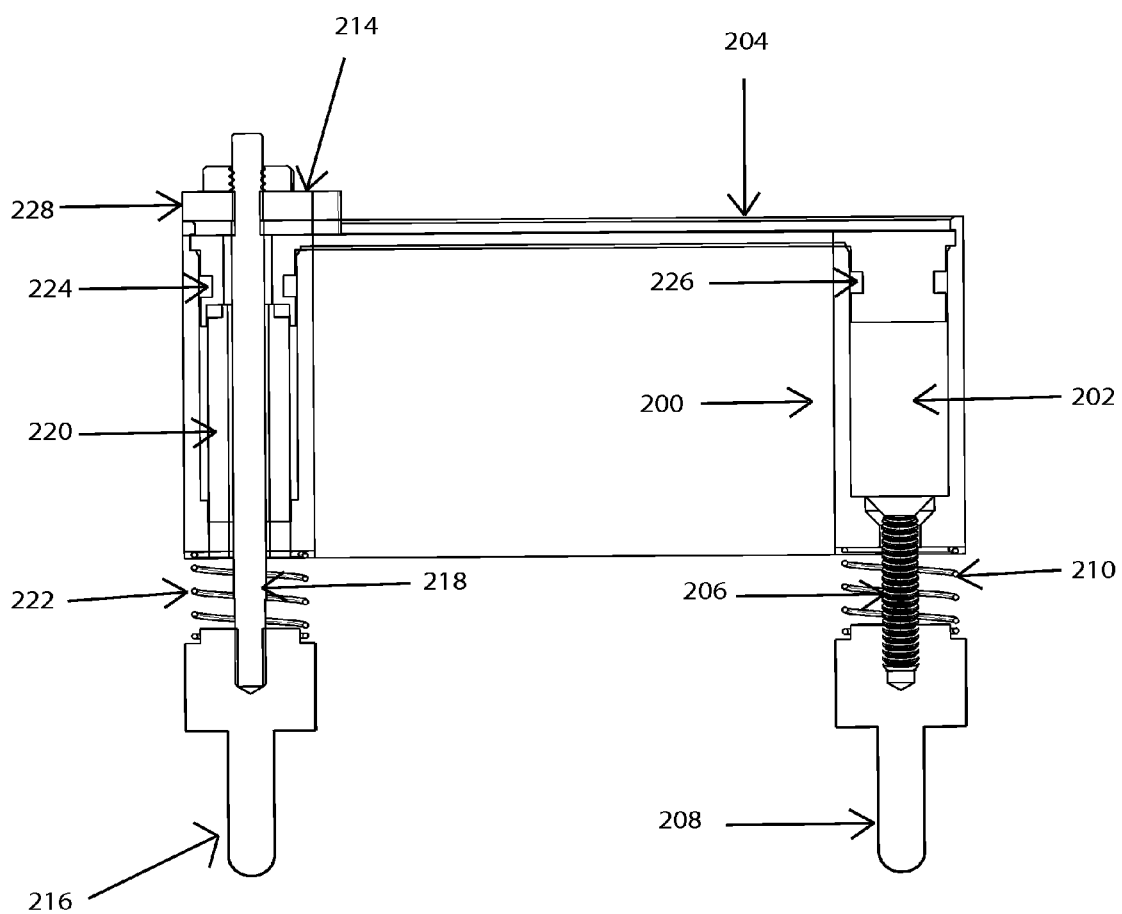
FIG. 2A is a schematic cross-sectional view of a biocide reservoir unit in the device of the present invention.
Figure 2B:
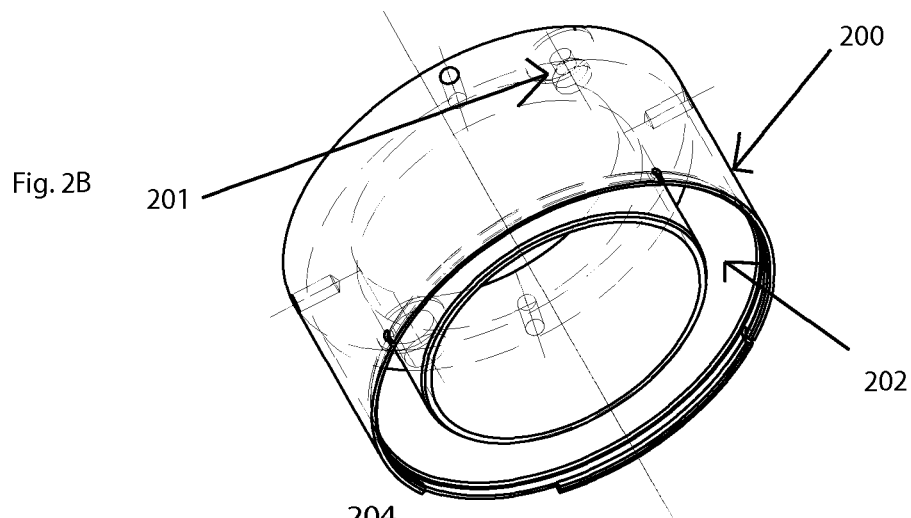
FIG. 2B is a bottom and side perspective unit of a biocide reservoir of the biocide reservoir unit of the present invention.
Figure 2C:
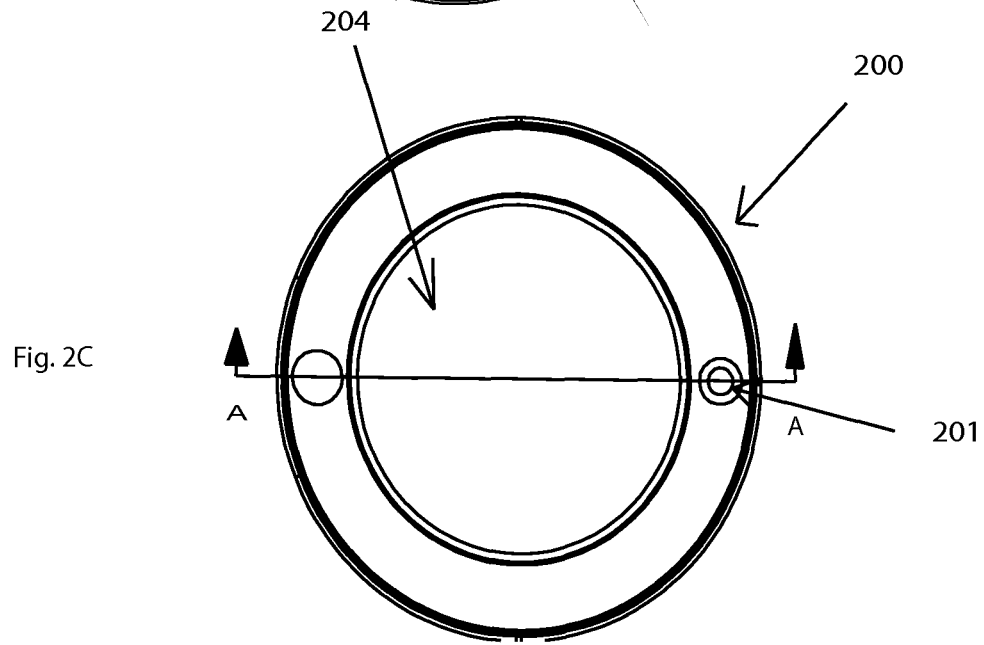
FIG. 2C is a top perspective view of the biocide reservoir lid of the biocide reservoir unit of the present invention.
Figure 2D:
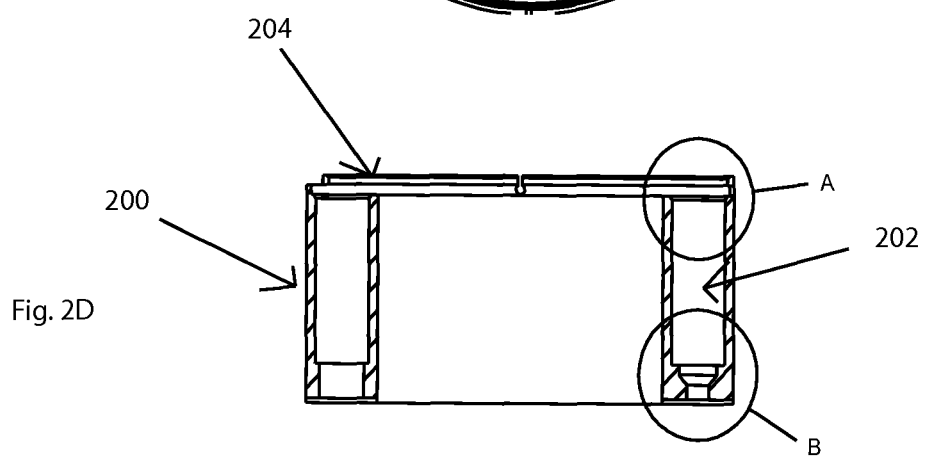
FIG. 2D is a cross-sectional view of the biocide reservoir of the biocide reservoir unit of the present invention.
Figure 2E:
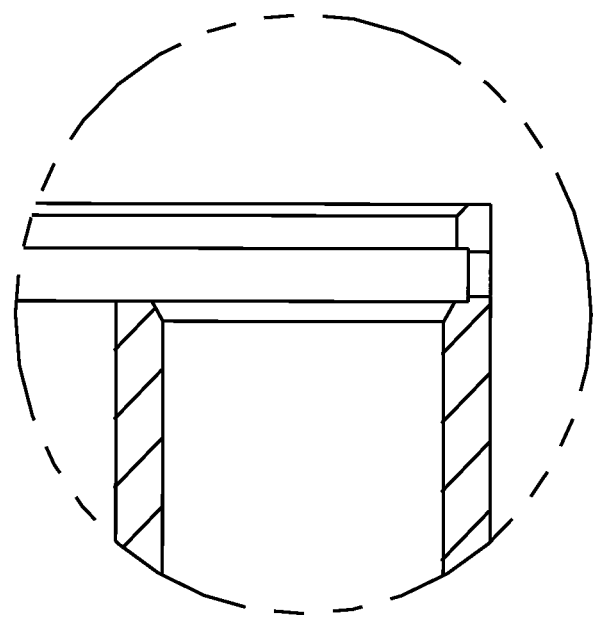
FIGS. 2E and 2F are detail views of one embodiment of the biocide outlet valve openings of the biocide reservoir of the present invention.
Figure 2F:
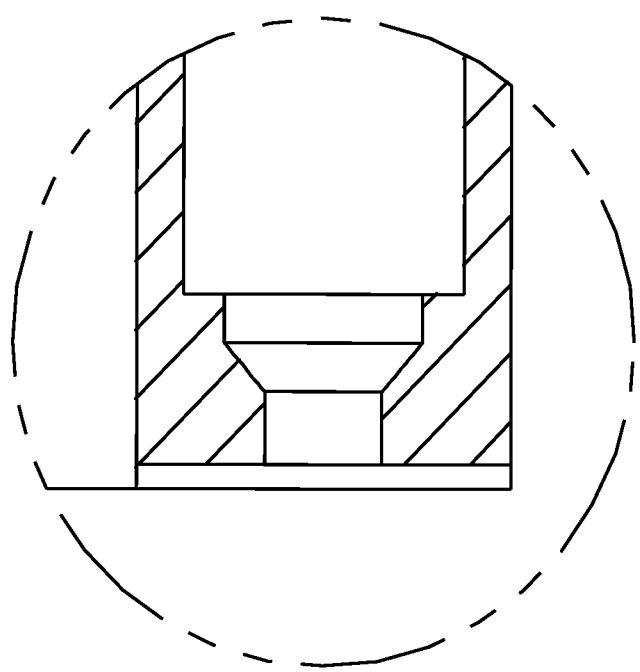

As shown in FIGS. 2A-2O, the biocide reservoir unit 200 may be implemented in a reservoir 202, covered with a removable lid 204 which securely snaps unto the reservoir unit 200, and having an interior reservoir 202 filled with biocides and/or solution of biocide. In a preferred embodiment, the reservoir unit comprises an outer sleeve and an inner sleeve arranged substantially concentric with respect to the outer sleeve and having a closable upper end and a closed lower end 203 which establish an annular reservoir space 202 filled with biocide matter, the reservoir unit further comprising a biocide outlet means and vent in fluid communication with the chamber. The inner sleeve defines a central opening in the reservoir unit which is configured and adapted to extend radially around the stirrer blades for rapid and even dispersal of the biocide matter. Details of a preferred embodiment of the biocide reservoir unit is shown in FIGS. 2B, 2C, 2D, 2E and 2F.) The toroid shape of the biocide reservoir unit increases the biocide volume that can be stored at a sufficient distance from certain optical sensors so not to interfere with measurements. By surrounding the stirrer propeller, it also acts like a Kort Nozzle and improves stirring and flushing efficiencies.

The biocide reservoir unit further has a biocide outlet valve 206 which can be implemented as flat head screw device with chemically resistant o-ring (e.g. silicon or viton) to make a water tight seal with a counter sunk hole in the bottom of the biocide reservoir unit 200. (See FIGS. 2D, 2E, and 2F for details of a preferred embodiment of the outlet valve.) When the push peg 208 is lifted by a ramp (See FIGS. 8A-8E) the screw 206 is lifted and the dense contents of the biocide reservoir unit are released. When the pushpeg (See FIGS. 2L, 2N) moves past the ramp, the valve spring 210 returns the screw and o-ring tightly into the counter sunk hole and closes the valve. Thus, the biocide valve compression spring 210 maintains a seal in the biocide valve 206 until it is compressed when the biocide valve pushpeg rides up the ramp during inner cup 56 rotation.

The biocide valve screw 206 threads into a hole in the top of the pushpeg 208. The peg is raised and lowered as it rides over or stops and starts on the top of the ramp 102 during the inner cup motion.

The biocide reservoir unit 200 further has a vent 212 covered by a vent lid locking means 214 which may be implemented as a simple nut to secure the vent lid in place. See FIG. 2K. The vent 212 is operated by a vent pushpeg 216 (See FIGS. 2N, 2P) which is actuated in the same fashion as the biocide valve push peg 208. It accepts a threaded push rod 218 at the top that moves up and down through the reservoir bushing 220 (See FIG. 2O). The vent push rod 218 connects the vent push peg 216 to the vent lid 214 and is preferably threaded on both ends. A vent compression spring 222 maintains a seal between the vent lid 214 and the reservoir lid 204 until it is compressed when the vent pushpeg rides up the ramp during inner cup 56 rotation. The vent bushing is preferably press fit with glue and preferably a permanent part of the reservoir. The vent bushing 220 makes a water tight seal with the reservoir lid 204 via a chemically resistant o-ring.

The vent and outlet valve permit concentrated solid biocide to be placed in the reservoir 202 that will gradually be dissolved by the ambient water introduced into the reservoir 202 when the valves are opened. By allowing the sampling environment to provide the water necessary to dissolve the concentrated biocide much larger inventories of biocide can be accommodated within a small volume.

Further disposed on the biocide reservoir unit 200 is an outer biocide reservoir lid o-ring groove 224 to form a water tight seal with reservoir unit's body; an inner biocide reservoir lid o-ring groove 226 which forms water tight seal with reservoir body and a vent lid 214 which forms a water tight seal against two holes in the reservoir lid located on both sides of the lid center. Preferably the vent lid 214 uses a soft pad or silicon grease on the bottom to form a seal. A preferred embodiment of the biocide reservoir lid is shown in FIGS. 2G, 2H, 2I and 2J.

The biocide 28 may include calcium hypochlorite pellets or powder, or copper chloride, salts of acids, various metal salts, and basically a very wide range of dry and water soluble chemicals for chamber 20 sterilization including Sodium dichloroisocyanurate dihydrate, trichloroisocyanuric acid etc.

Figure 3A:
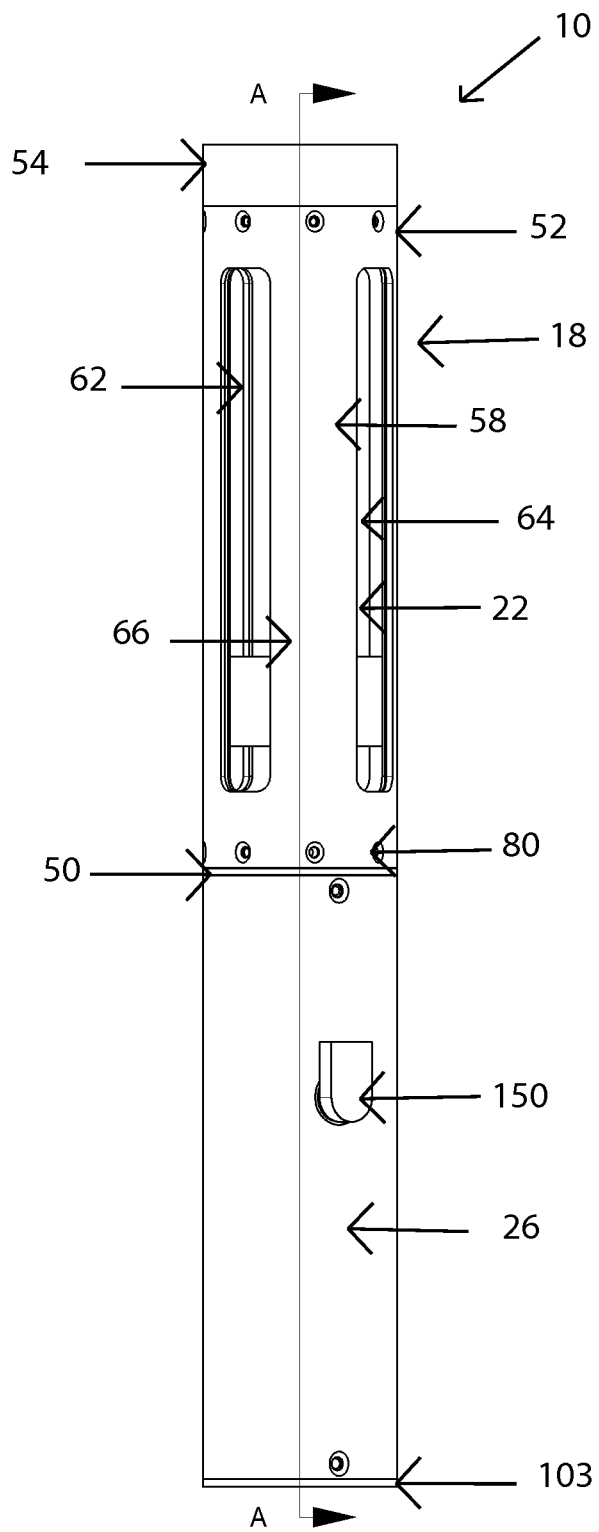
Figure 3B:
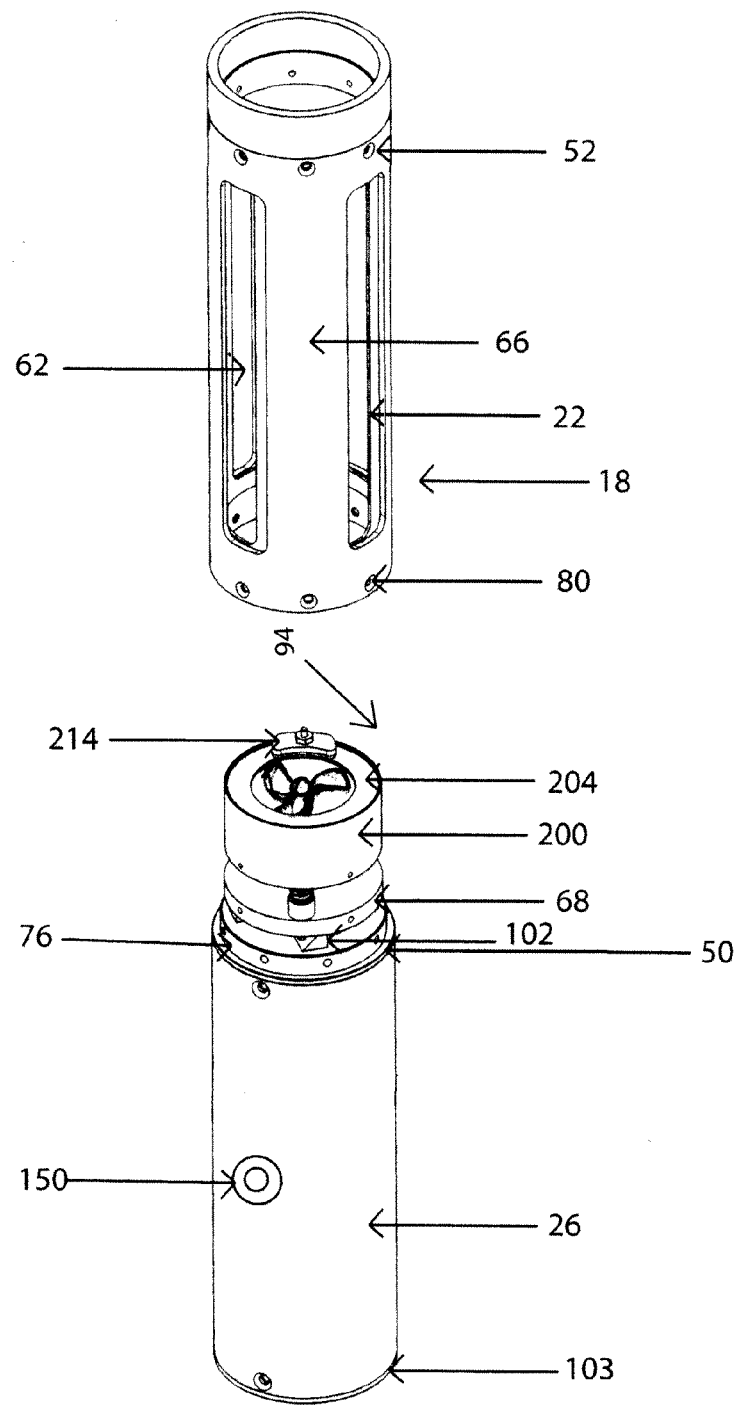
Figure 3E:
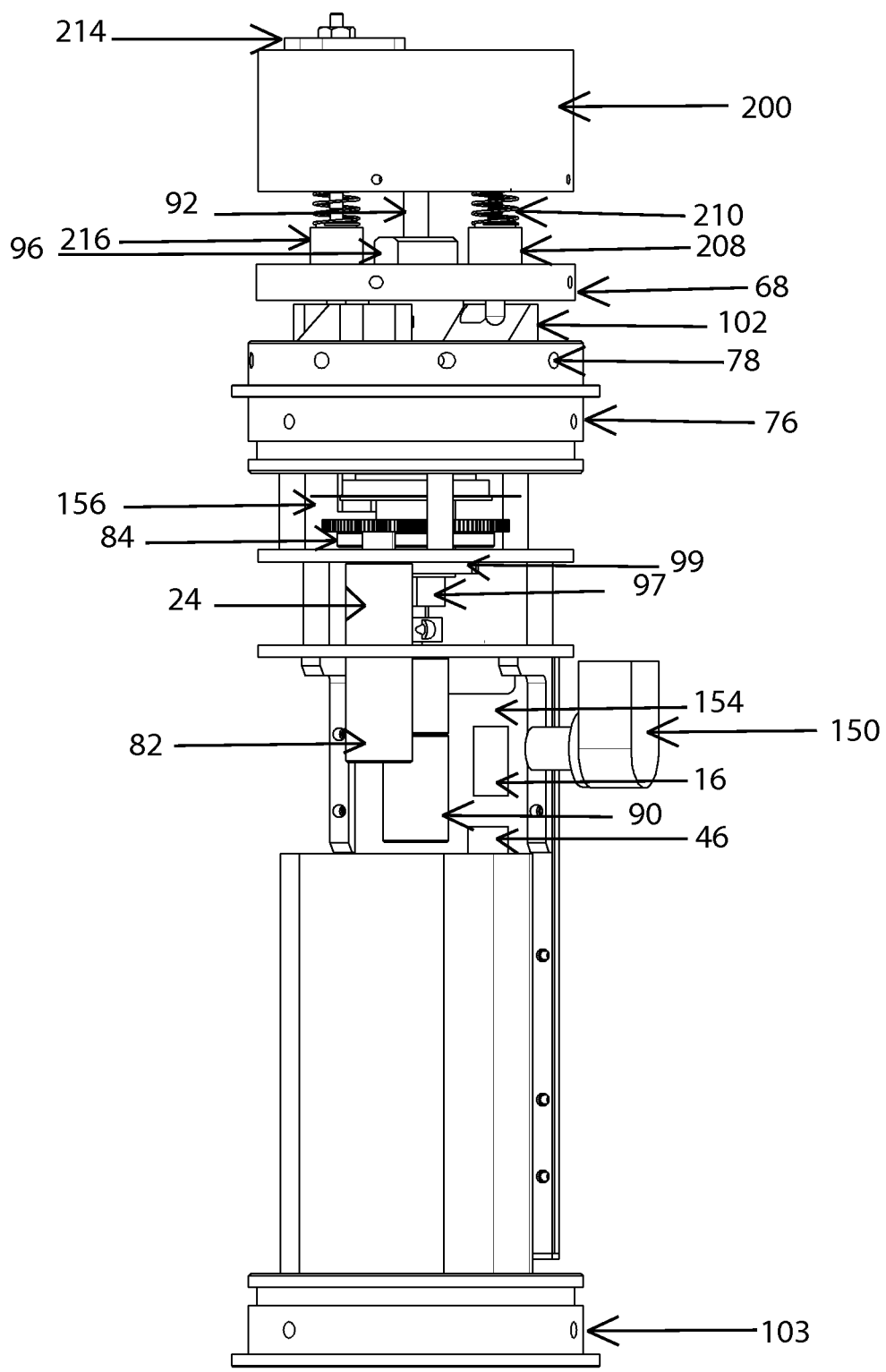
FIGS. 3E is a longitudinal semi cross-section of the monitoring device of the present invention.

The autonomous device 10 regulates biocide dosing into the chamber 20 using an actuated biocide reservoir unit vent/outlet valve mechanism as shown in FIGS. 3C, 3D and 3E and described in detail in further paragraphs. The operation of the biocide reservoir unit's vent/outlet valve is controlled by the actuator 24 in synchrony with opening/closing of the shutters 22 of the chamber 20. As will be presented further, when the shutters 22 in the chamber 20 are nearly closed, the actuator will gradually open the biocide reservoir unit's outlet valve for a programmed duration. When the outlet valve open period expires, the shutters 22 in the chamber 20 move to the completely closed position thereby moving the push peg 216 off of the ramp and closing the biocide reservoir unit's outlet valve.

Thus one push peg 216 directly opens a vent on the top of the reservoir unit 200 and the other opens a biocide outlet valve 206 at the bottom of the reservoir. During a biocide introduction cycle, the vent is first opened by the rotating inner cup mechanism to vent the reservoir 202 thereby allowing any gas to escape and ambient water to enter. The inner cup is further rotated such that the push peg 216 runs off the ramp and the vent is closed via the spring 222. Further rotation opens and closes the biocide valve 206 in the same manner the vent is controlled. This allows the release of the dense biocide solution or slurry contained within. After closing the biocide valve 206 the stirrer is run to mix the biocide throughout the closed sampling chamber. By adding a second ramp located opposite the first, the vent and valve can be opened simultaneously to increase the release rate of the biocide.

The anti-fouling environment within the chamber 20 is then stirred briefly to evenly disperse the biocide inside the sensor envelope 18, e.g. in the chamber 20. It is contemplated in the scope of the present invention, that the autonomous device 10 can accommodate more than one biocide source with different biocides with each reservoir having its own vent and biocide release valves.

The controller (microprocessor) 16 is preprogrammed prior to deployment of the autonomous device 10 to control operation of the autonomous device 10. The microprocessor 16 also supervises serial communication of the autonomous device 10 with a telemetry and data collection system 44, to periodically dispatch data thereto when and if needed.

The deployment parameters including sampling frequency, biocide dosing frequency, as well as biocide dispense time and amount, stirring/flushing duration, as well as sequence of operations, are preferably embedded in the microprocessor 16 in a lab prior to deployment of the autonomous device 10. Thus, the autonomous device 10 independently controls the operation of the sensors 14, as well as the mechanics and electrical components. The microcontroller 16 further is "responsible" for data recording in the memory 46, and for synchronization of all the components operations over several months deployment.

The telemetry and data collection system 44 can periodically request the data stored on the non-volatile memory 46 of the autonomous device 10. A serial user interface 48, shown in FIG. 1, may be used in the autonomous device 10 to accommodate telemetered control and data acquisition.

It is clear that although it is possible to provide continuous on-line external telemetry with a remote host computer, the autonomous device 10 preferably runs independently for as long as it is intended, by programming the microcontroller 16 before deployment, and therefore constitutes an independently controlled device which can operate without external control for extended time deployment periods.

Referring to FIG. 3A-3F, the autonomous device 10 includes the sensor envelope (housing) 18 coupled at an end 50 thereof with the electronics and battery housing 26. The sensor envelope 18 is adapted at the end 52 thereof to accommodate the sensor instrument 54 which has individual sensors 14 and which may be a single probe or a multiprobe environmental sensing instrument, such as for example 6-series sensors, which may be fitted into the sensor housing 18 which may have an annular cross-section shown in FIG. 3F.

Figure 4:
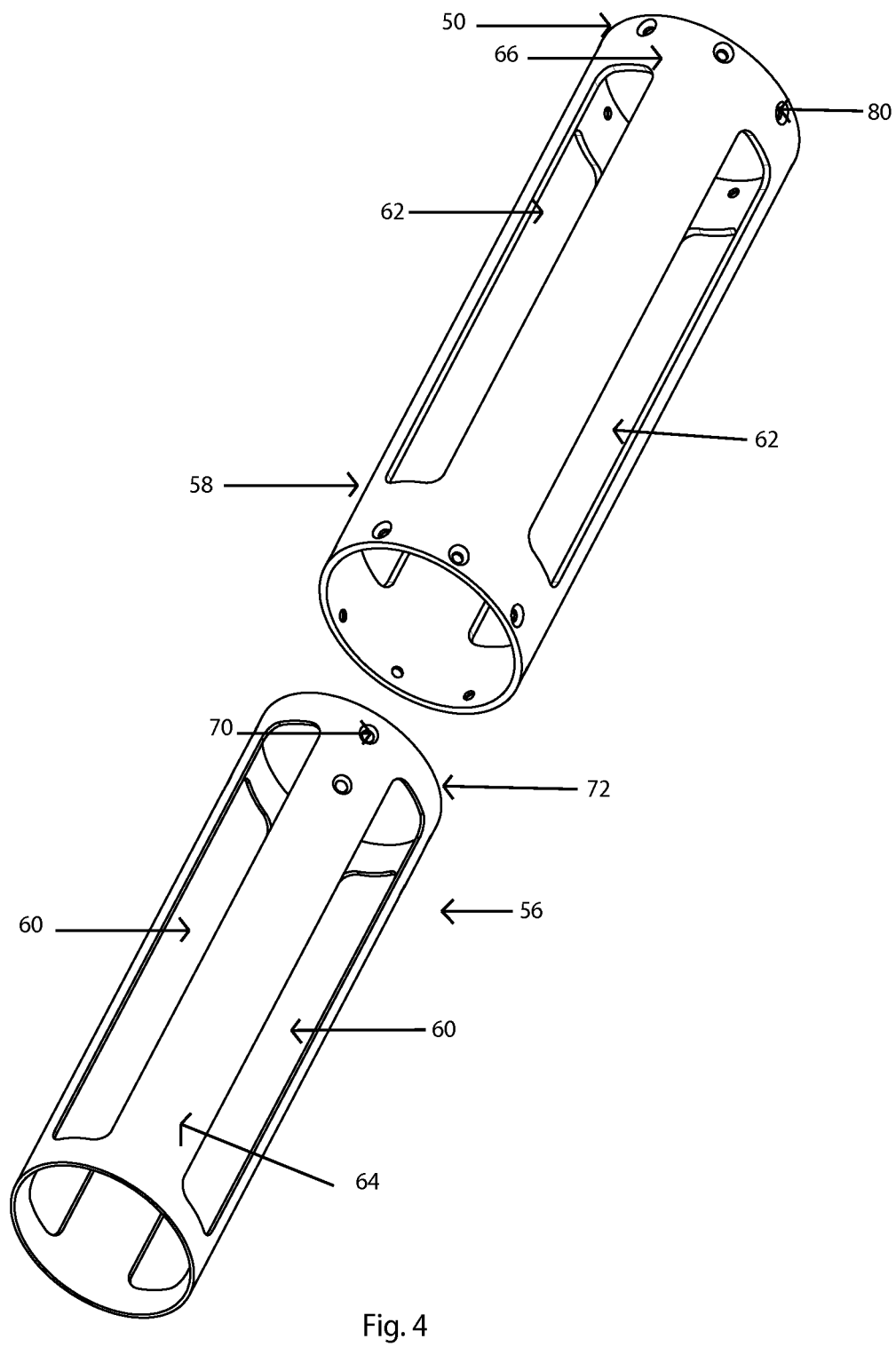
FIG. 4 is an expanded view of the interrelated inner and outer cups.
Figures 5, 6:
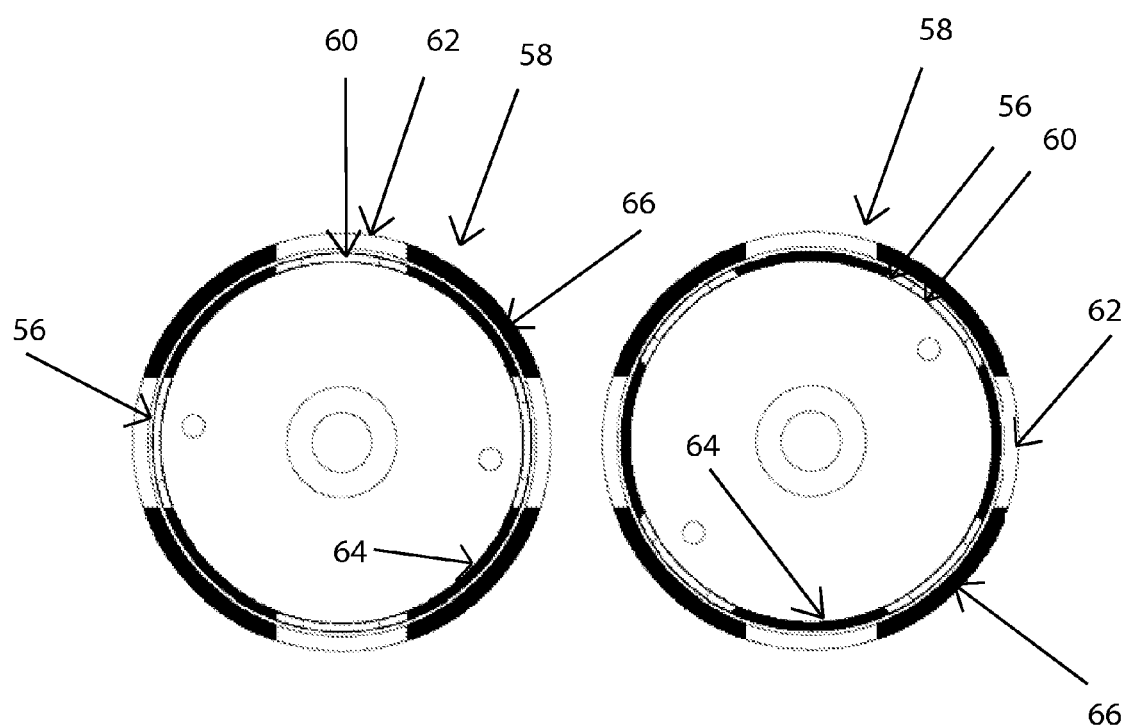
FIGS. 5 and 6 show schematically a cross-section of interrelated inner and outer cups with the sampling chamber completely closed (FIG. 5) and open (FIG. 6)

Although other implementations are contemplated in the present invention, as an example, the sensor housing 18 may be devised as a two-layer structure, which, as best shown in FIGS. 4, 5, 6 includes an inner cup 56 and an outer cup 58 disposed concentrically each with respect to the other. The inner cup 56 has a plurality of inner cup openings 60, while the outer cup 58 has a plurality of outer cup openings 62 which correspond in shape and dimension to the inner cup openings 60. As shown in FIG. 4, although there are four inner cup openings 60 and four outer cup openings 62 on each respective cup 56 and 58, a different number of openings also may be contemplated in the scope of the present invention. The inner cup openings 60 and outer cup openings 62 are formed in the wall 64 of the inner cup 56 and of the wall 66 of the outer cup 58, respectively and at predetermined positions which are selected in correspondence each to the other.

In operation, when the water from the aquatic environment is to enter into the chamber 20, the actuator 24 (shown in FIG. 3F) rotates the inner or outer cups relative each to the other to align the inner cup opening 60 to the outer cup opening 62 in order to open the chamber 20 to the ambient aquatic environment. However, when the chamber 20 is to be closed, or partially closed, the actuator 24 rotates the inner or outer cups relative each to the other to controllably change the extent of overlapping between the inner cup opening 60 and outer cup opening 62 to either leave small openings in the chamber 20 or completely close the chamber by overlapping the inner cup openings 60 with the wall 66 of the outer cup between the openings 62.

Figure 3F:
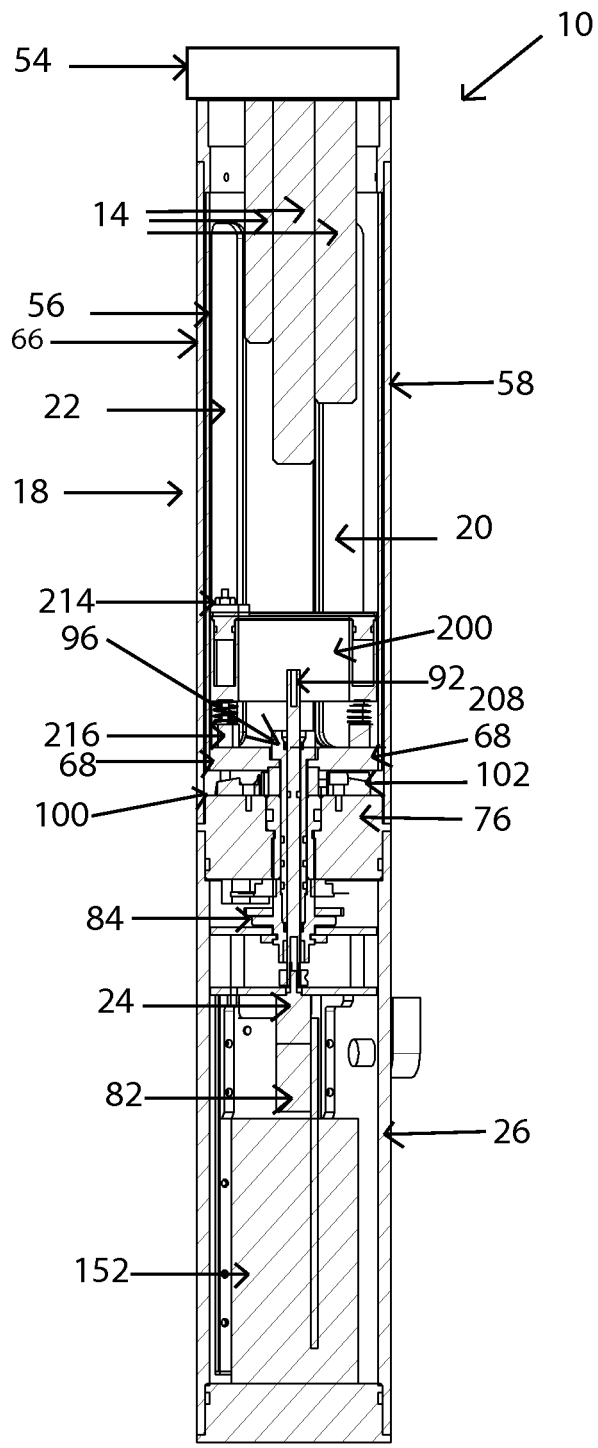
FIG. 3F is a schematic representation of one embodiment of the mechanical/electrical control mechanism in the device of the present invention.

As best shown in FIGS. 3F and 4, the inner cup 56 is mounted to a support disk or base plate 68 by means of fasteners protruding through holes 70 formed at the edge 72 of the inner cup 56 (best shown in FIGS. 4) and the openings 74 formed at the support disk 68 (best shown in FIG. 3F). The outer cup 58 is mounted to the chamber bulk-head 76 (best shown in FIG. 3F) which has openings 78 positioned circumferentially around the perimeter thereof in alignment with the openings 80 at the edge 50 of the outer cup 58 as best shown in FIGS. 3E and 3F The actuator 24 includes a motor 82 shown in FIG. 3E, which rotates the support disk or base plate 68 (e.g. the inner cup 56) through a gear mechanism 84 (See FIG. 7D) and a system of limit switch cams 86, schematically shown in FIG. 3E. The inner cup base plate 68 is rotated in accordance with instruction received by the motor 82 from the programmable microprocessor 16. When the inner cup base plate 68 is rotated by the motor 82 through the gear mechanism 84 and the limit switch cams 86, the inner cup 56 mounted thereon also rotates relative to the outer cup 58 which remains immovable. In accordance with instructions received by the motor 82 from the programmable microprocessor 16, and as best shown in FIGS. 3F, the inner cup 56 may be displaced to a position relative to the outer cup 58 so that either the inner cup openings are disaligned with the outer cup openings, e.g. the openings are covered by the walls of the other cup, as shown in FIG. 5. Alternatively, the inner cup openings and outer cup openings may be aligned each with respect to the other for complete opening of the chamber 20, as shown in FIG. 6. There are other relative dispositions possible (although not shown), when there is a partial overlap between the openings and walls of another cup, to leave narrow slits opened in the sensor envelope to regulate flow of the water through the openings.

Figure 11A:
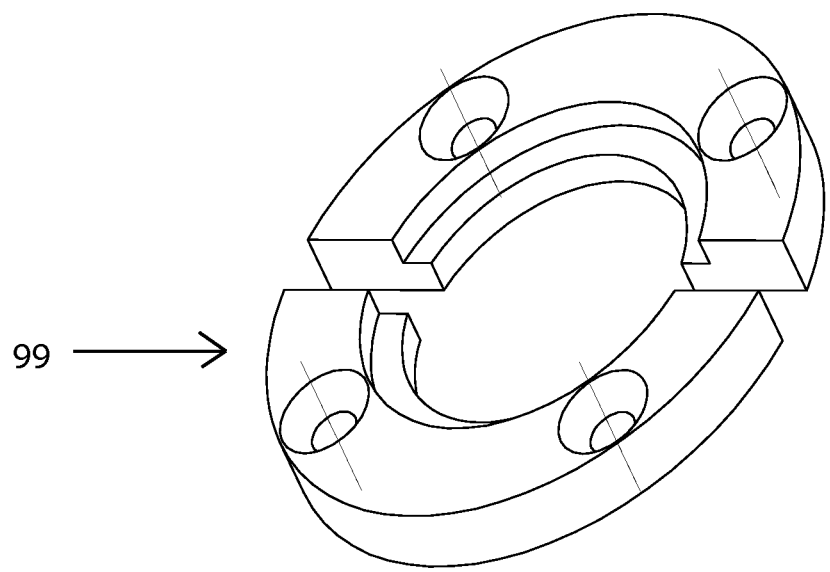
FIGS. 11A-11B bearing housing retainer.
Figure 11B:
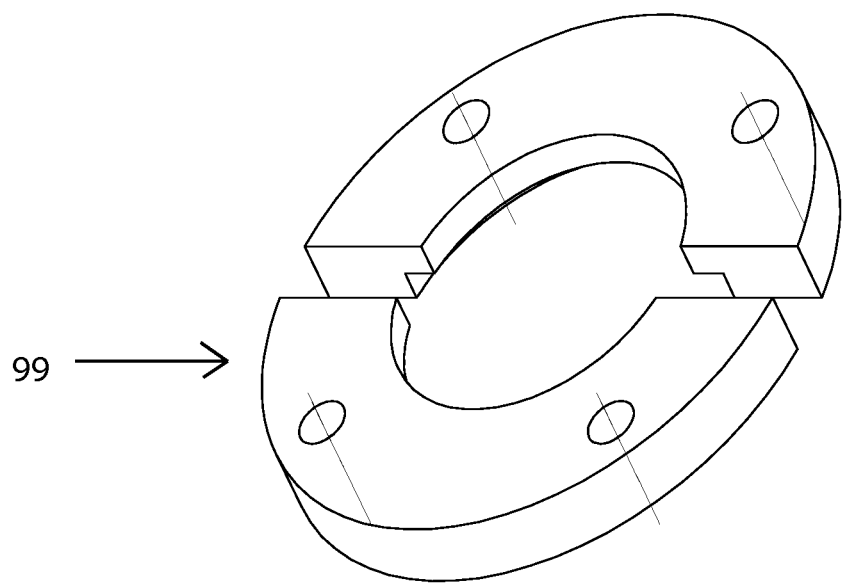
Figure 12A:
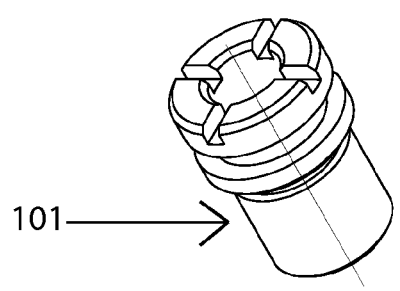
FIGS. 12A-12C are perspective views of the outer shaft bushing of the present invention.
Figure 12B:
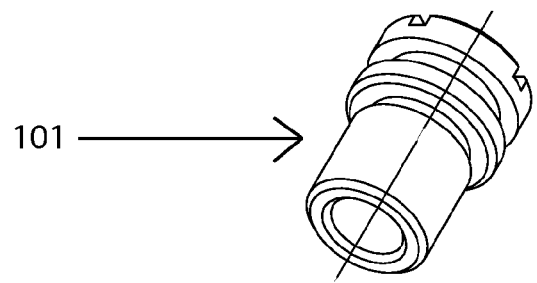
Figure 12C:
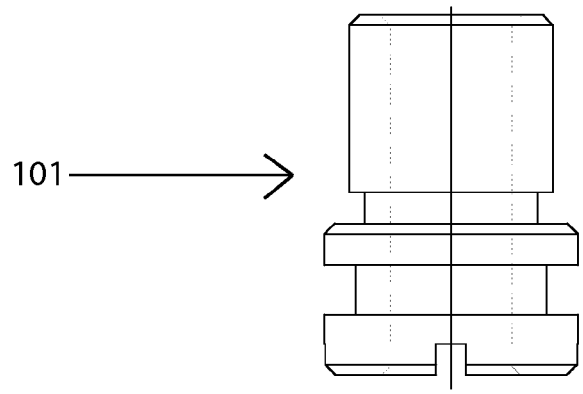
Figures 13A, 13B:
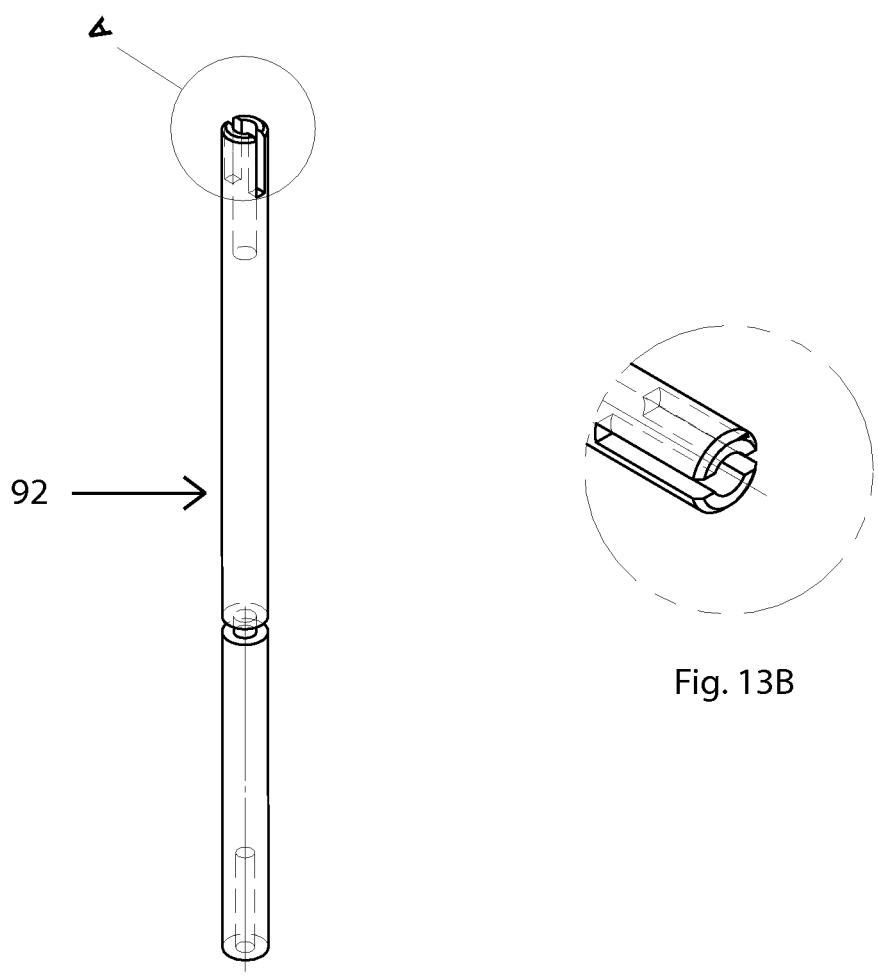
FIGS. 13A-13B are perspective views of the stirrer (inner) shaft.
Figure 16:
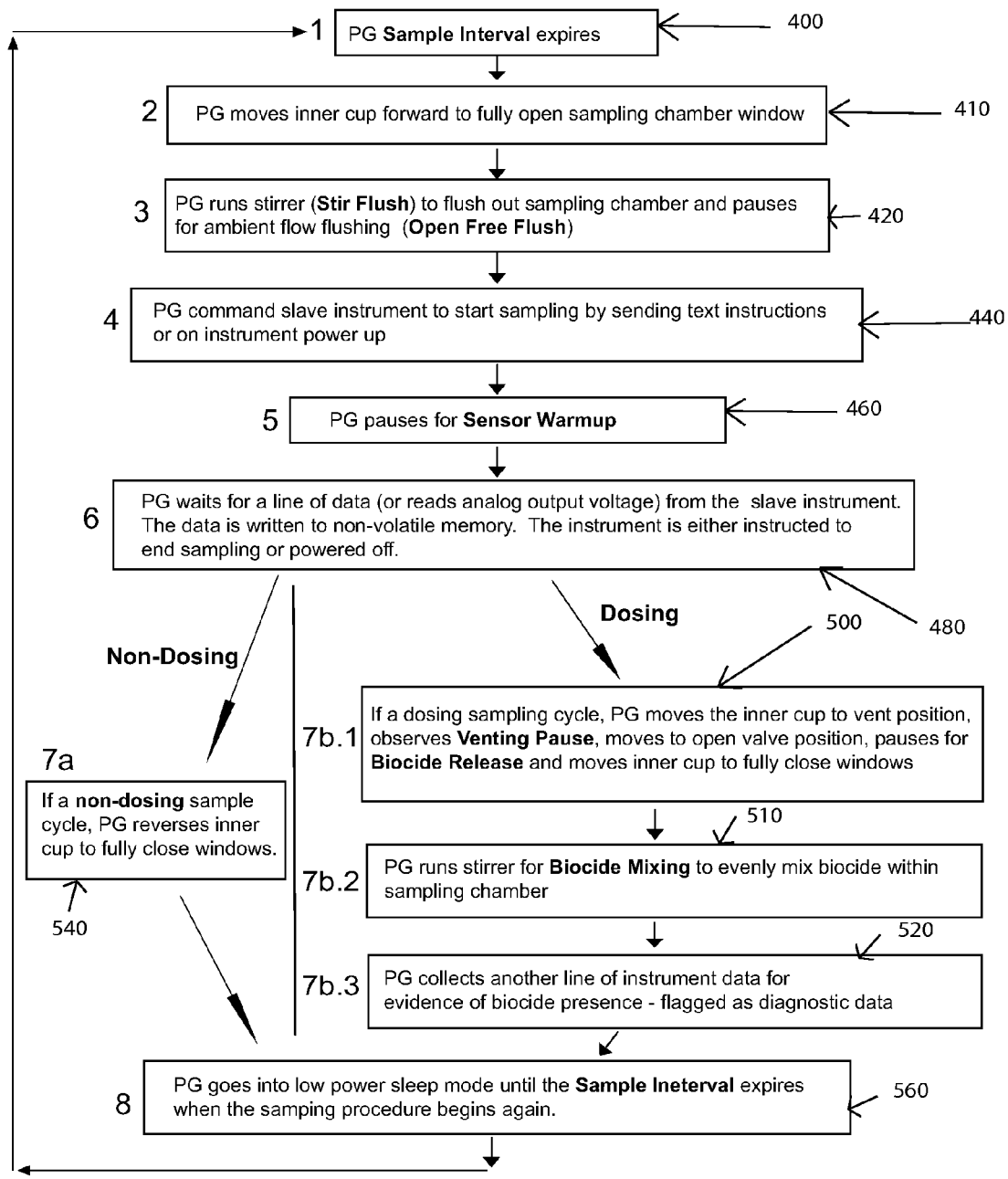
FIG. 16 is a flow-chart diagram of the software embedded in the microprocessor in the monitoring device of the present invention.

The actuator 24 may also have another motor 90 positioned on a stirrer shaft (inner shaft) 92 which has a stirrer 94 (shown in FIG. 3F) at the other end thereof. Alternatively, the motor 82 may perform the function of both rotating the inner cup, as well as the function of rotating the stirrer 94 by using a gear train between the motor (outer) 82 shaft and the stirrer shaft 92. For the single motor implementation, the mechanical component is changed, as well as the program "sewn-in" the microprocessor adjusted to specify an alternative schedule of operation. The stirrer shaft 92 (FIG. 3F) passes through the cup rotator shaft 96, as best shown in FIGS. 9A-10F. The cup rotator shaft 96 penetrates the chamber bulkhead via a bearing housing 97 (See FIGS. 10A-10F) retained on the chamber bulk head using the bearing housing retainer 99. (See FIGS. 11A-11B). The cup rotator shaft 96 is in turn coupled to the gear mechanism 84 and is directly rotated by the motor 82 through the gear mechanism 84. Optical encoder is used to count steps of rotation. The encoder counts are fed to the Motor Control Unit that processes the counts to control inner cup position. The retaining clip 99 (FIGS. 11A and 11B) holds the bearing housing in place and helps align the shafts. The shaft bushing 101 (FIGS. 12A-12C) goes down middle of the chamber bulk head 76 and the outer shaft 96 rotates inside the shaft bushing 101.

The biocide reservoir unit 200 is mounted relative to the inner cup base plate 68 as best shown in FIG. 3D with the stirrer rotating between the walls of the reservoir unit as shown in FIG. 3B.

As best shown in FIG. 3D, the chamber bulk-head 76 carries on the upper surface 100 thereof one to four ramp units 102 disposed circumferentially at the outer periphery of the chamber bulk head 76. As best shown in FIGS. 8A-8E each ramp unit 102 includes a ramp portion 104, a horizontal top portion 106, a void portion 108 cut off abruptly from the horizontal top portion 106, and an opening 110 passing through the entire height of the ramp unit 102. Each ramp unit 102 is secured to the upper surface 100 of the chamber bulk head 76 by a fastener (not shown) inserted into the opening 110 that allows the ramp to pivot when the inner cup is reveresed and the push pegs contact the back side of the ramp.

The biocide reservoir unit's push pegs 208 and 216, penetrate the inner cup base plate 68 as shown in FIG. 3D with the top of the push pegs in contact with the retaining springs 210, 222 and the bottom in contact with the ramp portion of the chamber bulk head 76. An illustration of one embodiment of the chamber bulk head is shown in FIGS. 14A-14D.

When the inner cup is rotated relative to the outer cup by means of rotating the inner cup base plate 68 by the motor 82, the bottom of the push pegs 208, 216, climb up along the ramp portion 104 of the ramp unit 102 thereby causing the compression of the springs 210, 218. This action causes the gradual lifting of the biocide reservoir unit's outlet valve 206 to dispense biocide into the sensor envelope 20.

When the inner cup base plate 68 is further rotated counterclockwise relative to the bulk-head 76, a relative displacement of the vent push peg 216 with regard to the ramp unit 102 is attained. Specifically when bottom of the vent push peg 216 has moved from the horizontal portion 106 to the void portion 108 of the ramp unit 102, the push peg 216 reciprocates down into the void 108 causing the vent push rod 218 to move up through the vent bushing 220 to vent accumulated pressure in the biocide reservoir 202 that may result when using biocides such as chlorine salts that release gas during dissolution. The opening of the vent also allows ambient water to replace the liquid lost through the biocide valve and to continue to dissolve more solid biocide inside the reservoir. A saturated solution of biocide is maintained inside the reservoir 202 until all the solid biocide is dissolved. Unlike using a liquid biocide, the reservoir unit 200 containing solid biocide has a very high biocide density—less space and more punch.

It is clear that by displacing the inner cup base plate 68, e.g. the inner cup 56 relative to the outer cup 58 mounted on the chamber bulk head 76, the control of the release of the biocide 28 from the reservoir 202 into the sensor envelope 20, is thus performed in complete synchronization with the sampling cycle of the autonomous device 10 and in synchronization with opening/closing of the sensor envelope 20.

By reducing the steepness of the ramp portion 104 of the ramp units 102, strain on the motors can be reduced. The size of the biocide dose is controlled by the duration the valve opening via density driven flow and the shape of the flat head screw. When the peg rides off the ramp, the spring quickly snaps the valve closed so the o-ring and screw head actually push biocide out in the form of a displacement pump Dosing depends on the duration of the valve opening and by the number of times the peg rides up and off the ramp. Additionally, the device of the present invention can reverse the inner cup so the peg just clears the pivoting ramp and then rides back up the ramp, pause on top of the ramp with the valve open and then rides off the ramp a second time. Furthermore, the efficiencies of both the density flow and the displacement flow can be adjusted by changing the geometries of parts (e.g. size and shape of the screw head, size of the hole the screw penetrates). In this manner the control of the release of the biocide 28 from the reservoir 202 may be controlled through programmed actuation of the motor 82 in accordance with the program embedded in the programmable microprocessor 16 prior to the deployment of the autonomous device 10 of the present invention.

Referring again to FIGS. 1, 3A, 3C, 3D and 3E, the autonomous device 10 includes a power and communication plug 150 which is a submersible and wet mattable plug, meaning it may be plugged in under the water. The power and communication plug 150 has a Y-connector which has one end thereof extending from the plug to the sensor instrument 14 to supply power and communication thereto, while the other end of the Y-connector is able to receive power from an external supply and to provide communication for external control (the user interface for PC programming in the lab prior to deployment), or to function to telemetry data to the remote telemetry and data collection system.

The pressure housing 26, having a rear bulk head 103 (See FIGS. 15A-15B) is coupled to the sensor housing 18, serves as mechanics, electronics and battery casing and may receive batteries 152 therein, as well as the drive motor 82, gear train 84. Also, the pressure housing 26 accommodates a second motor 90 and a printed circuit board 154 (shown in FIG. 3E) with the programmable microprocessor 16 and the non-volatile memory 46 providing that all electrical, electronic and mechanical components of the autonomous device 10 are kept within the housing 26 sealed from water intrusion.

An optical sensor 156, shown in FIG. 3E, may be used to "count" the position of the outer shaft/inner cup 82 in order to control its position. The optical sensor is disposed in proximity to the gear train 84 to count the number of slits on the gear disks. The number of slits is processed in the microprocessor 16 which controls the motor 82 accordingly.

Referring to FIG. 16, the sequence of operations of the autonomous device (ProbeGuard) 10 controlled by the programmable microprocessor 16 is presented as follows. The programmable microprocessor 16 has software 160 embedded therein which synchronizes the operation of all parts of the autonomous device 10 to run the sampling cycle of the sensors 14 in a predetermined order and in complete synchronization with mechanical motion of the inner cup versus outer cup, as well as in synchronization with the release of the biocides from the reservoir 202 into the sensor chamber 20.

As presented in FIG. 16, when a previous sample interval "i" expires in block 400 (the inner and outer cup windows are staggered such that the sampling chamber is closed as shown in FIG. 5), the microprocessor 16 issues an instruction for the autonomous device 10 to pass the logic to block 410 in accordance with which the inner cup 56 assumes the position with relation to the outer cup 58 where the inner cup opening 60 and outer cup opening 62 overlap, as presented in FIG. 6, to open the sensor chamber 20 to the ambient environment to the fullest extent. At this position, the logic of the microprocessor 16 writes the action code, time and date to a log file as needed. One of skill in the art understands that every action need not be logged. Further the information or logic passes to block 420 where with the completely opened sensor chamber 20, the microprocessor 16 instructs the motor 90 to actuate the stirrer 94 for "f" seconds to flush out water contained in the sensor chamber 20 and pauses "a" seconds for ambient flow flushing.

By the motion of the stirrer 94, the water contained in the sensor chamber 20 before the shutters were opened in block 410, is completely replaced with the fresh water from the aquatic environment 12. Rotational movement of the stirrer 94 when the windows of the sensor chamber 20 are opened creates-vertical flow, e.g. the turbulence, resulting in pulling water surrounding the device through the open windows and underneath the biocide reservoir unit and pushing that fresh ambient water toward the above mounted sensor probes. The stirrer works for a predetermined time duration, for example 10-60 seconds, to replace water in the sensor chamber 20.

Upon completion of the stirring action, the logic flows to block 440 and the microprocessor 16 pause for a programmed duration for continued ambient flow flushing and then when configured in "serial mode", instructs the sensor instrument 54 to start a sample sequence sending a text command(s) to the slave instrument e.g. RS232 user interface port, and writes action code and time stamp to the log file. Alternatively, some serial instruments and most analog instruments can be configured to make measurements and report text data or the analog voltage upon the application of power. To accommodate this configuration (power up mode), the device is equipped with the microprocessor (16) controlled power output. In serial mode, the microprocessor 16 sends text commands to the slave instrument to initiate sampling, observes a programmed pause for sensor equilibration and or warm up and then collects a line of data. The instrument is then commanded to stop sampling and return to low power sleep mode. If no data is delivered by the instrument a "data collection timeout" will elapse and the device will record the error and begin the countdown to the next sample. In power up mode, the device applies power to the slave instrument, observes the sensor warmup time 460, and waits for a line of serial data or reads the sensor's analog output voltage. The instrument is then powered off. If no data is returned before the timeout elapses, the error is logged and the device returns to its programmed sample/sleep schedule 480.

If a non-dosing sample cycle, the device reverses inner cup to fully close windows. 540

Upon the sample sequence (sampling time period) being completed, the microprocessor 16 activates block 500 and instructs the motor 82 to close the sensor chamber 20 to the extent sufficient to open the biocide reservoir unit's outlet valve 206 for "d" seconds (for example 5-15 seconds). During this action, the microprocessor 16 writes action code and time stamp to the log file as needed and other time stamped actions and performance data (e.g. motor current, system voltage, etc). When the reservoir unit's outlet valve 206 opens, the biocide 28 is released from the reservoir 202 by a gravity assist flow, and the microprocessor 16 instructs the motor 82 to close shutters (inner and outer cup openings) thereby completely causing the biocide reservoir unit's outlet valve 206 to close and writes action code and time stamp to the log file. This dosing action can be repeated by reversing the inner cup such that the biocide reservoir unit's push peg is moved back in front of the pivoting ramp and then the inner cup is immediately moved forward until the push peg is once again on top of the ramp and the valve is opened. As on the initial dose, the programmed period for the density flow is observed and the inner cup is moved to fully close sampling chamber windows.

At this time, the sensor chamber 20 contains an anti-fouling environment created by releasing the biocide from the reservoir 202 and diluting it in the water in the sensor chamber 20. Further, the microprocessor 16 instructs the motor 90 to run the stirrer 94 for "m" seconds (for example 5-10 seconds) as instructed in the logic block 510. By rotating the stirrer 94 in the chamber 20 containing the anti-fouling environment (e.g. the biocide diluted in the water), the biocide is evenly dispersed in the chamber 20 to immediately surround the surface of the sensors 14 and to "sterilize" the environment surrounding the sensors 14. In block 510, the logic writes the action code and time stamp to the log file.

The logic optionally flows to block 520 where the device collects another line of instrument data for evidence of biocide presence—flagged as diagnostic data.

The logic further flows to block 560 where the microprocessor 16 puts the device into a predetermined "sleep" time interval "i" (15 minutes through 12 hours) and writes the action code and time stamp to the log file. Upon the "sleep" mode being completed, the logic loops back to block 400 and the process repeats through blocks 410 through 560.

Although the autonomous device 10 is sensor independent, meaning that a very wide array of environmental sensors can be used therewith, the sensors envisioned in the scope of this invention may include sensors basically for all environmental measurements such as, for example, optical sensors for measurement of oxygen, chlorophyll, pH, fluorescence sensors, sensors for measuring temperature, salinity, etc.

The present device may use a wide variety of biocides and powders including calcium hypochlorite, trichloroisocyanuric acid in the form of pellets or powders. Copper salts or chelated copper is also one of the choices for the biocide as it is highly soluble in water and forms a very dense solution. As has been presented in previous paragraphs, the biocide reservoir could be segmented and equipped with additional valves such that it could accommodate different biocides. One implementation of the multiple biocide arrangement is by use of a multiconcentric reservoir defining different annular regions containing different biocides. Alternatively, each biocide reservoir may be opened or closed in a programmable manner in a specific sequence with regard to other biocide reservoirs to provide for a great flexibility in dosing the water in the chamber in a predetermined desired manner.

Materials for construction of the different embodiments of the device of the present invention suggest readily to one of skill in the art. The biocide reservoir unit should be constructed from chemical resistant materials such as PVC or polycarbonate. For instance, the outer shaft may be constructed of polyether ether ketone thermoplastic; the shaft retainer of PVC; the inner (stirrer) shaft of titanium. Corrision resistance is considered for parts exposed to seawater (titanium for small parts, 316 SS for parts requiring strength and plastics for larger parts or ones that are not exposed to high stress)

In choosing materials, it is understood that marine organisms attach themselves to some metals and alloys more readily than they do to others. Steels, titanium and aluminum will foul readily. Copper-based alloys and coatings (90% Cu-10% Ni and 70% Cu-30% Ni, respectively), including Cu—Ni, have very good resistance to biofouling, and are preferred materials for construction and/or coating of the different embodiments of the invention such as the casing and the inner and outer cups which are typically exposed to marine environments depending on the cost considerations. It is understood though that the inside of the chamber is kept clean by the biocide. Coarse copper screen (⅛" mesh) may be wrapped around the outside of the sampling chamber to prevent fish and crabs from getting stuck inside.

It is also contemplated that fouling release coatings commonly known in the art may be used to impact additional biofouling resistance to the device of the present invention. Usually made of polymers (plastics), these coatings are non-toxic and are thought to have a natural resistance to biofouling by creating a low surface tension and having a low glass transition temperature. Polymers utilized in these coatings are silicones and fluoropolymers and ethyl vinyl acetates.

While the disclosure has been described with reference to exemplary embodiments, it will be understood by those skilled in the art that various changes may be made and equivalents may be substituted for elements thereof without departing from the scope of the disclosure. In addition, many modifications may be made to adapt a particular situation or material to the teachings of the disclosure without departing from the essential scope thereof. Therefore, it is intended that the disclosure not be limited to the particular embodiment disclosed as the best mode contemplated for carrying out this disclosure, but that the disclosure will include all embodiments falling within the scope of the appended claims. Documents including patents and non patent references cited herein are expressly incorporated by reference.

What is claimed:

1. A device with bio-fouling control for autonomous monitoring of a fluid environment, comprising:
    at least one sensor unit operationally controllable to operate in accordance with a predetermined sampling cycle, the sampling cycle including at least one sampling time period followed by an anti-fouling treatment time period,
    a sensor envelope having at least one closable window positioned in a surrounding relationship with the at least one sensor unit and defining a chamber containing the at least one sensor unit,
    at least one source of an anti-fouling matter contained in the chamber the source of anti-fouling matter comprising an outer sleeve and at least one inner sleeve arranged substantially concentric with respect to the outer sleeve and having a closable upper end and a closed lower end which establish an annular reservoir space filled with biocide matter, the source of anti-fouling matter further comprising a biocide outlet means and vent in fluid communication with the chamber, and
    a preprogrammed control unit operatively coupled to the sensor envelope and the at least one source of the anti-fouling matter,
    wherein the preprogrammed control unit actuates the said sensor envelope to control the opening and closing of said at least one closeable window to provide fluid communication between the at least one sensor unit and a fluid during the at least one sampling time period, and further activates the biocide outlet means of the at least one source of the anti-fouling matter to create an anti-fouling environment in the chamber during the anti-fouling treatment time period.

2. The device of claim 1, wherein the at least one window being opened, under control of the preprogrammed control unit, during the at least one sampling time period to permit the fluid inside the sensor envelope in contact with the at least one sensor unit, and wherein the at least one window is controllably closed during the anti-fouling treatment time period to maintain the anti-fouling environment inside the sensor envelope.

3. The device of claim 2, wherein the preprogrammed control unit synchronizes opening/closing of the at least one window of the chamber with the controllable release of the biocide matter in the chamber.

4. The device of claim 2, wherein the chamber includes an outer cup and an inner cup positioned in concentric relationship with the outer cup, the outer cup having an outer cup wall and a plurality of outer cup openings formed at predetermined positions on the outer cup wall, and the inner cup having an inner cup wall and a plurality of inner cup openings formed at predetermined positions on the inner cup wall,
the inner and outer cups having a first relative disposition during the at least one sampling time period and a second relative disposition during the anti-fouling treatment time period,
wherein in the first relative disposition between the inner and outer cups, respective ones of the plurality of inner cup openings and of the plurality of outer cup openings are positioned to overlap each other, and
wherein in the second relative disposition between the inner and outer cups, the respective inner cup and outer cup openings are displaced each from the other in a controlled manner.

5. The device of claim 4, wherein during the anti-fouling treatment time period, the displacement between the respective inner cup and outer cup openings is synchronized with the release of the biocide matter by the preprogrammed control unit.

6. The device of claim 4, further comprising an actuation unit operatively coupled to either of the inner and outer cups to establish a respective one of the first and second relative dispositions therebetween in accordance with instructions received from the preprogrammed control unit.

7. The device of claim 6, wherein the preprogrammed control unit further includes a microprocessor preprogrammed prior to deployment of the device in the fluid environment.

8. The device of claim 7, further comprising a non-volatile memory, wherein data obtained from the at least one sensor unit is stored in the non-volatile memory under control of the preprogrammed microprocessor.

9. The device of claim 8, wherein the device further includes an interface port, the data being dispatched periodically from the non-volatile memory to a telemetry and data collection system via a communication link established between the device and the telemetry and data collection system.

10. The device of claim 1, wherein the biocide matter includes at least one salt selected from a group consisting of: calcium hypochlorite pellets, calcium hypochlorite powder, copper chloride, salts of acids, metal salts, dry chemicals, water soluble chemicals.

11. The device of claim 4, further comprising:
a first and second co-axial supporting disks positioned in the chamber and rotationally displaceable about an axis thereof, the first and second co-axial supporting disks being spaced each from the other along the axis,
wherein the inner cup is mounted on the first supporting disk, and wherein the outer cup is mounted on the second supporting disk,
a plurality of ramp units positioned circumferentially on a surface of the second supporting disk a predetermined distance each from another between the first and second supporting disks; and
a vent and valve mechanism mounted on the first supporting disk in a controllable contact with the at least one source of the anti-fouling matter, the valve mechanism being actuated by interaction with a respective one of the plurality of ramp units in accordance with a relative disposition between the first and second supporting disks to control opening of the vent or valve when the first and second co-axial supporting disks are rotationally displaced under control of the preprogrammed control unit.

12. The device of claim 11, further comprising a flushing unit inside the chamber operating to remove the anti-fouling environment therefrom upon completion of the anti-fouling treatment time period prior to the at least one sampling time period.

13. The device of claim 11, further comprising:
a casing connected to the sensor envelope at one end thereof, the casing having an internal cavity fluidly separated from the chamber of the sensor envelope,
batteries and an actuator mechanism received within the internal cavity of the casing, and
wherein the preprogrammed controller is received in the casing.

14. The device of claim 2, wherein the inner sleeve of the at least one source of anti-fouling matter defines a central opening which is configured and adapted to extend radially around stirrer blades of a propeller for rapid and even dispersal of biocide matter.

15. A method for bio-fouling control of an autonomous device for monitoring a fluid environment, comprising the steps of:
forming a sensor envelope for at least one sensor unit,
positioning the at least one sensor unit into a chamber defined within the sensor envelope,
programming a control unit prior to deployment of the autonomous device in the fluid environment,
deploying the autonomous device having the preprogrammed controller unit embedded therein in the fluid environment,
opening the chamber to the fluid environment under control of the preprogrammed control unit to establish fluid communication between a fluid and the at least one sensor unit,
sampling the fluid,
upon completion of the sampling during at least one sampling time period, closing the chamber, and
releasing, under the control of the preprogrammed control unit, at least one biocide matter from a biocide reservoir unit comprising an outer sleeve and an inner sleeve arranged substantially concentric with respect to the outer sleeve and having a closable upper end and a closed lower end which establish an annular reservoir space filled with biocide matter, the reservoir unit further comprising a biocide outlet means and vent in fluid communication with the chamber to create an anti-fouling environment therein, thereby exposing the at least one sensor unit to the anti-fouling environment during an anti-fouling treatment time period.

16. The method of claim 15, further comprising the steps of:

upon completion of the anti-fouling treatment time period, opening the chamber, and replacing the anti-fouling environment in the chamber with the fluid.

17. The method of claim 15, further comprising the step of:

during the anti-fouling treatment time period, activating stirring of the anti-fouling environment to evenly disperse the at least one biocide matter within the chamber.

18. The method of claim 15, further comprising the steps of:

recording data acquired during the at least one sampling period in a memory block of the autonomous device, establishing a communication link between the autonomous device and a data collection system, and sending the recorded data from the memory to the data collection system for further processing.

19. The method of claim 15, further comprising the steps of:

preprogramming the control unit prior to the deployment of the autonomous device to embed therein operation parameters selected from the group consisting of: sampling frequencies, biocide dispense time, biocide dispense amount, stifling duration of the biocide in the chamber, duration of flushing of the anti-fouling environment from the chamber, duration of the sampling time period, duration of the anti-fouling treatment time period, and parameters for synchronized operation of the autonomous device.

20. A device with a bio-fouling control for monitoring a fluid environment, comprising:

at least one sensor unit operating in accordance with a predetermined sampling cycle including at least one sampling time period followed by an anti-fouling treatment time period, a sensor envelope having at least one closable window, for the at least one sensor unit, the at least one sensor unit being disposed in a chamber defined by the sensor envelope, at least one biocide reservoir comprising an outer sleeve and inner sleeves arranged substantially multiconcentric with respect to the outer sleeve and having a closable upper end and a closed lower end which establish an annular reservoir space filled with biocide matter, the at least one biocide reservoir further comprising biocide outlet means and vents in controlled fluid communication with the chamber, an actuating unit operatively coupled to the at least one biocide reservoir, and a controller unit controlling the actuating unit in a programmable manner, wherein, during the anti-fouling treatment time period, upon completion of the at least one sampling time period, the actuating unit, under the control of the control unit, activates release of the biocide matter from the at least one biocide reservoir in a controlled fashion through a valve mechanism to create an anti-fouling environment in the chamber, thereby exposing the at least one sensor unit to the anti-fouling environment upon completion of the at least one sampling time period to substantially prevent and eliminate bio-fouling in an immediate surrounding of the at least one sensor unit.

* * * * *